(12) United States Patent
Lu et al.

(10) Patent No.: US 7,192,970 B2
(45) Date of Patent: Mar. 20, 2007

(54) NONCYCLIC 1,3-DICARBONYL COMPOUNDS AS DUAL PPAR AGONISTS WITH POTENT ANTIHYPERGLYCEMIC AND ANTIHYPERLIPIDEMIC ACTIVITY

(75) Inventors: Xian-Ping Lu, Guangdong (CN); Zhibin Li, Guangdong (CN); Chenzhong Liao, Guangdong (CN); Leming Shi, Guangdong (CN); Zhende Liu, Guangdong (CN); Zhiqiang Ning, Guangdong (CN); Song Shan, Guangdong (CN); Tuo Deng, Guangdong (CN); Baoshun Ma, Guangdong (CN)

(73) Assignee: Chipscreen Biosciences, Ltd. (CN)

( * ) Notice: Subject to any disclaimer, the term of this patent is extended or adjusted under 35 U.S.C. 154(b) by 238 days.

(21) Appl. No.: 10/713,722

(22) Filed: Nov. 14, 2003

(65) Prior Publication Data

US 2004/0138211 A1 Jul. 15, 2004

Related U.S. Application Data

(60) Provisional application No. 60/429,294, filed on Nov. 26, 2002.

(51) Int. Cl.
*A61K 31/47* (2006.01)
*C07D 215/38* (2006.01)
*C07D 215/44* (2006.01)

(52) U.S. Cl. .................... 514/312; 546/153; 546/157
(58) Field of Classification Search ............. 546/153, 546/157; 514/312
See application file for complete search history.

(56) References Cited

U.S. PATENT DOCUMENTS

| | | | |
|---|---|---|---|
| 6,369,055 | B1 | 4/2002 | Jeppesen et al. |
| 2002/0065268 | A1 | 5/2002 | Jeppesen et al. |
| 2002/0082292 | A1 | 6/2002 | Sahoo et al. |
| 2002/0103242 | A1 | 8/2002 | Sahoo et al. |
| 2005/0020684 | A1 | 1/2005 | Brooks et al. |

FOREIGN PATENT DOCUMENTS

| | | |
|---|---|---|
| WO | WO94/13650 * | 6/1994 |
| WO | WO 97/25042 | 7/1997 |
| WO | WO 00/08002 | 2/2000 |
| WO | WO 01/55085 | 8/2001 |
| WO | WO 02/26729 A2 | 4/2002 |

OTHER PUBLICATIONS

Buckle, D.R., Bioorganic & Medicinal Chemistry, Letters, vol. 6, No. 17, pp. 2127-2130, 1996.*
T.M. Wilson, et al, "The PPAR's from orphan receptors to drug discovery," J. Med. Chem. 2000 43:527-550, A.
Chawla, et al, Nuclear receptors and lipid physiology "Opening the X-files", Science, 2001, vol. 294, 1866-1870.
Keller & Wahli, Peroxisome Proliferator-Activated Receptors A Link Between Endocrinology and Nutrition, TEM vol. 4, No. 9, 1993, 291-296.
Wang YX et al, Peroxisome-Proliferator-Activated Receptor o Activaaaaaates Fat Metabolism to Prevent Obesity, Cell, Apr. 18, 2003, vol. 113, 159-170.
Lee, Ch et al, Transcriptional Repression of Atherogenic Inflammation: Modulation by PPAR's, Science, vol. 302, Oct. 17, 2003, pp. 453-457.

* cited by examiner

*Primary Examiner*—D. Margaret Seaman
(74) *Attorney, Agent, or Firm*—Buchanan Ingersoll & Rooney, P.C.

(57) ABSTRACT

Disclosed are the preparation and pharmaceutical use of novel noncyclic 1,3-dicarbonyl compounds of formula I, wherein ring A, ring B, $R^1$, $R^2$, $R^3$, $R^4$, $R^5$, X, Y, Z, Q, Ar and n are as defined in the specification. These compounds, as peroxisome proliferator-activated receptor (PPAR) dual agonists for both RXR/PPARgamma and RXR/PPARalpha heterodimers, are useful in the treatment and/or prevention of type 2 diabetes and associated metabolic syndrome such as hypertension, obesity, insulin resistance, hyperlipidemia, hyperglycemia, hypercholesterolemia, atherosclerosis, coronary artery disease, and other cardiovascular disorders

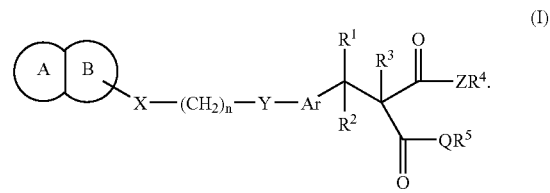

(I)

16 Claims, 10 Drawing Sheets

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: PCR primer

<400> SEQUENCE: 1
acgtgcttcc tgcttcatag a                                              21

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
cctgagatta gccacctccc                                                20

<210> SEQ ID NO 3
<211> LENGTH: 41
<212> TYPE: DNA
<213> ORGANISM: Artificial Sequence
<220> FEATURE:
<223> OTHER INFORMATION: PPAR response element

<400> SEQUENCE: 3
gatcctctcc tttgacctat tgaactatta cctacatttg a                        41

<210> SEQ ID NO 4
<211> LENGTH: 28
<212> TYPE: DNA
<213> ORGANISM: Artificial Sequence
<220> FEATURE:
<223> OTHER INFORMATION: PCR primer

<400> SEQUENCE: 4
ggggtacctg cttcagcagc gtgttcga                                       28

<210> SEQ ID NO 5
<211> LENGTH: 28
<212> TYPE: DNA
<213> ORGANISM: Artificial Sequence
<220> FEATURE:
<223> OTHER INFORMATION: PCR primer

<400> SEQUENCE: 5
gctctagatg ttggcagtgg ctcaggac                                       28

NONCYCLIC 1,3-DICARBONYL COMPOUNDS AS DUAL PPAR AGONISTS WITH POTENT ANTIHYPERGLYCEMIC AND ANTIHYPERLIPIDEMIC ACTIVITY

Priority is herein indicated from U.S. Provisional Application Ser. No. 60/429,294, filed Nov. 26, 2002.

FIELD OF THE INVENTION

The present invention relates to the preparation and pharmaceutical use of noncyclic 1,3-dicarbonyl analogs. More particularly, the present invention relates to novel compounds of the general formula I, their preparation methods, their pharmaceutical compositions and their use for treatment and/or prevention of conditions mediated by nuclear receptors, in particular the RXR and PPAR heterodimers.

The present compounds are useful in treatment and/or prevention of type 2 diabetes and associated metabolic syndrome such as hypertension, obesity, insulin resistance, hyperlipidemia, hyperglycemia, hypercholesterolemia, atherosclerosis, coronary artery disease, and other cardiovascular disorders.

BACKGROUND OF THE INVENTION

Metabolic syndrome, including type 2 diabetes and associated complications such as obesity and dyslipidemia, are of major impact on social and economic significance. Although anti-diabetic treatments improve insulin resistance, they offer little protection from eminent cardiovascular risk associated with type 2 diabetes. Therefore, there is the need for developing new treatments that have insulin-sensitizing and cholesterol/triglycerides-lowering effects.

Diabetes mellitus is a polygenic disorder affecting a significant portion of the people in the world. It is divided into two types. In type 1 diabetes, or insulin-dependent diabetes mellitus (IDDM), patients produce little or no insulin, the hormone that regulates glucose utilization. In type 2 diabetes, or noninsulin dependent diabetes mellitus (NIDDM), patients often have plasma insulin levels that are at the same compared to nondiabetic humans; however, these patients have developed a resistance to the insulin stimulating effect on glucose and lipid metabolism in the main insulin-sensitive tissues, i.e., muscle, liver and adipose tissues, and the plasma insulin levels are insufficient to overcome the pronounced insulin resistance. Type 2 diabetes consists of over 90% of all diabetes. It is a metabolic disorder characterized by hyperglycemia leading to secondary complications such as neuropathy, nephropathy, retinopathy, hypertriglyceridemia, obesity, and other cardiovascular diseases generally referred as metabolic syndrome.

The treatment generally prescribed for type 2 diabetes has been a combination of diet, exercise, and oral hypoglycemic agents, commonly sulfonylurea and biguanides. However, sulfonylurea therapy has many problems associated with primary and secondary failure of efficacy, incidence of hypoglycemia, and obesity. The biguanides therapy can induce lactic acidosis, nausea and diarrhea. Hence, a drug that can control plasma glucose tightly without significant side effects would be an important addition to diabetes therapy. Recently, a class of compounds termed thiazolidinediones has been shown to reduce hyperglycemia by sensitizing insulin action without additional insulin secretion, and without causing undesirable hypoglycemia, even at elevated doses. Their effect is proposed to be a result of initiation and modulation of adipocyte differentiation by agonist activity of PPARgamma. This class of compounds that is able to activate PPARgamma has been demonstrated clinically effective in treatment of type 2 diabetes (AVANDIA from GSK and ACTOS from Lilly/Takeda). Although the exact link from activation of PPARgamma to change in glucose metabolism, most notably a decrease in insulin resistance in muscle, has not yet been clarified, the link is via free fatty acids in such that activation of PPARgamma induces lipoprotein lipase, fatty acid transport protein and acyl-CoA synthetase in adipose tissue but not in muscle cells. This effect, in turn, reduces the concentration of free fatty acids in plasma dramatically, leading to eventual switch from fatty acid oxidation to glucose oxidation in high metabolic state of tissues, such as skeletal muscle and other tissues, due to substrate competition and pathway compensation. That results in a decreased insulin resistance in those tissues. Further, activation of PPARgamma modulates a subset of genes in controlling glucose and energy homeostasis, which leads to decrease blood glucose level (T. M. Wilson et al. "The PPARs: from orphan receptors to drug discovery" *J. Med. Chem.* 2000 43:527–50; A. Chawla et al. "Nuclear receptors and lipid physiology: Opening the X-files". *Science* 2001 294:1866–70)

Despite the advances made with the thiazolidinedione class of antidiabetes agents, serious unacceptable side effects including cardiac hypertrophy, hemodilution and liver toxicity have limited their clinical use. In the United States and Japan, several cases of liver damage and drug-related deaths due to liver damage have been reported. Further, PPARgamma-selective ligands induce adipocyte differentiation and white fat accumulation that leads to obesity, an important factor linking directly to the onset or the consequence of type 2 diabetes. Such unwanted effects will eventually compromise the insulin-sensitizing benefit of PPARgamma ligands. Hence, there is a definite need for a safe and efficacious agent for the treatment of type 2 diabetic patients that possesses dual activities of insulin-sensitizing as well as lowering white adipose deposition by regulating free fatty acids and triglycerides contents.

PPARgamma is a member of ligand-activated nuclear hormone receptor superfamily and expressed primarily in adipose tissues. A class of ligands named fibrates that are known to have triglyceride- and cholesterol-lowering activity activates another member of this family, the PPARalpha, which is mainly expressed in tissues such as liver. PPARalpha stimulates peroxisomal proliferation that enhances fatty acid oxidation, leading to reduced fatty acids level in blood (Keller and Wahli: *Trends Endocrin Metab* 1993, 4:291–296). Most recently, PPARdelta was reported to modulate lipid metabolism in which PPARdelta serves as a widespread regulator of fat burning. In vitro, activation of PPARdelta in adipocytes and skeletal muscle cells promotes fatty acid oxidation and utilization. Targeted activation of PPARdelta in adipose tissue in animals where PPARalpha is much less expressed, specifically induces expression of genes required for fatty acid oxidation and energy dissipation, which in turn leads to improved lipid profiles and reduced adiposity. Importantly, these animals are completely resistant to both high-fat diet-induced and genetically predisposed (Lepr(db/db)) obesity. Acute treatment of Lepr(db/db) mice with a PPARdelta agonist depletes lipid accumulation. In parallel, PPARdelta-deficient mice challenged with high-fat diet show reduced energy uncoupling and are prone to obesity (Wang Y X et al., Cell 2003 Apr. 18;113(2): 159–70). The transcriptional repression of atherogenic inflammation by ligand-activated PPARdelta was also reported, which further indicates the importance of PPAR-delta in combating cardiovascular diseases (Lee, C H et al., Science 302:453–457, 2003).

The PPARs form heterodimers with Retinoid X Receptor (RXR). The RXR/PPAR heterodimers thus play an important role in controlling cellular events such as glucose and lipid homeostasis, and adipocyte differentiation. Several classes of new chemical compounds were reported to have PPARalpha and gamma dual activities that are beneficial in the treatment and/or prevention of metabolic syndromes in animal and in human (US 2002/0065268 A1, U.S. Pat. No. 6,369,055 B1, WO01/55085A1, WO97/25042, WO02/26729 A2, a WO00/08002). However, dual agonists of the compounds having PPARalpha and delta or PPARalpha and gamma, or PPARdelta and gamma activities could offer a new opportunity for additional benefits against type 2 diabetes as well as cardiovascular complications with improved safety profiles.

SUMMARY OF THE INVENTION

One aspect of the present invention is directed to a compound of formula I

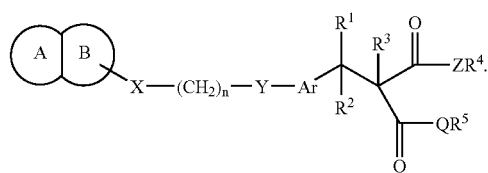

wherein
ring A, fused to ring B, represents a 5–6 membered cyclic ring, which may optionally contain one or more heteroatoms selected from oxygen, sulfur or nitrogen atoms and may optionally be substituted with one or more halogen, hydroxy, nitro, cyano, alkyl, alkenyl, alkenynyl, aralkyl, heteroarylalkyl, aminoalkyl, alkoxyalkyl, aryloxyalkyl, aralkoxyalkyl, hydroxyalkyl, thioalkyl, heterocyclyl, alkoxy, aryl, aryloxy, aralkoxy, heteroaryl, heteroaryloxy, heteroaralkoxy, acyl, acyloxy, amino, alkylamino, arylamino, or aralkylamino; the ring A may be saturated or contain one or more double bonds;

ring B, fused to ring A, represents a 5–6 membered cyclic ring, which may optionally contain one or more heteroatoms selected from oxygen, sulfur or nitrogen atoms and may optionally be substituted with one or more halogen, hydroxy, nitro, cyano, alkyl, alkenyl, alkenynyl, aralkyl, heteroarylalkyl, aminoalkyl, alkoxyalkyl, aryloxyalkyl, aralkoxyalkyl, hydroxyalkyl, thioalkyl, heterocyclyl, alkoxy, aryl, aryloxy, aralkoxy, heteroaryl, heteroaryloxy, heteroaralkoxy, acyl, acyloxy, amino, alkylamino, arylamino, or aralkylamino; the ring B may be saturated or contain one or more double bonds or may be aromatic;

X and Y are independently O, S, or $NR^6$ wherein $R^6$ represents hydrogen or $C_{1-3}$ alkyl;

Z represents O, S, or $NR^7$ wherein $R^7$ represents hydrogen, alkyl, aryl, or arylalkyl;

Q represents O, S, or $NR^7$ wherein $R^7$ represents hydrogen, alkyl, aryl, or arylalkyl;

$R^1$, $R^2$ and $R^3$ are independently H, alkyl, alkenyl, alkenynyl, aralkyl, heteroarylalkyl, aminoalkyl, alkoxyalkyl, aryloxyalkyl, aralkoxyalkyl, hydroxyalkyl, thioalkyl, heterocyclyl, OH, halogen, alkoxy, aryl, aryloxy, aralkoxy, heteroaryl, heteroaryloxy, heteroaralkoxy, acyl, acyloxy, amino, alkylamino, arylamino, or aralkylamino;

$R^4$, $R^5$ are independently H, alkyl, alkenyl, alkenynyl, aralkyl, heteroarylalkyl, heterocyclyl, aryl, or heteroaryl;

Ar represents arylene, hetero arylene, or a divalent heterocyclic group each of which can optionally be substituted with one or more halogen, $C_{1-6}$ alkyl, amino, hydroxy, $C_{1-6}$ alkoxyl or aryl;

n is an integer ranging from 1 to 6.

In another aspect of the invention, novel synthetic intermediates of formula II are synthesized, wherein ring A, ring B, X, Y, Ar and n are as defined previously, and T is —CHO or —$R^1$C=C(COOMe)$_2$, wherein $R^1$ is as defined previously.

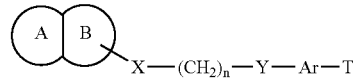

In another aspect of the present invention, a pharmaceutical composition is made by formulating at least one of the compounds of the general formula I, and/or a pharmaceutically acceptable salt thereof and a pharmaceutically acceptable carrier or diluent.

In another aspect of the present invention, a method is provided for treatment and/or prevention of type 2 diabetes and associated metabolic syndromes such as hypertension, obesity, insulin resistance, hyperlipidemia, hyperglycemia, hypercholesterolemia, atherosclerosis, coronary artery disease, and other cardiovascular disorders.

In a further aspect of the invention, the compounds of formula I are used for treating type 2 diabetes and associated complications in a patient and as selective agonists for RXR/PPARgamma and RXR/PPARalpha, or RXR/PPARdelta and RXR/PPARalpha, or RXR/PPARgamma and RXR/PPARdelta heterodimers.

The contents of the patents and publications cited herein and contents of documents cited in these patents and publications are hereby incorporated herein by reference to the extent permitted.

DETAILED DESCRIPTION OF THE INVENTION

Figure 1:
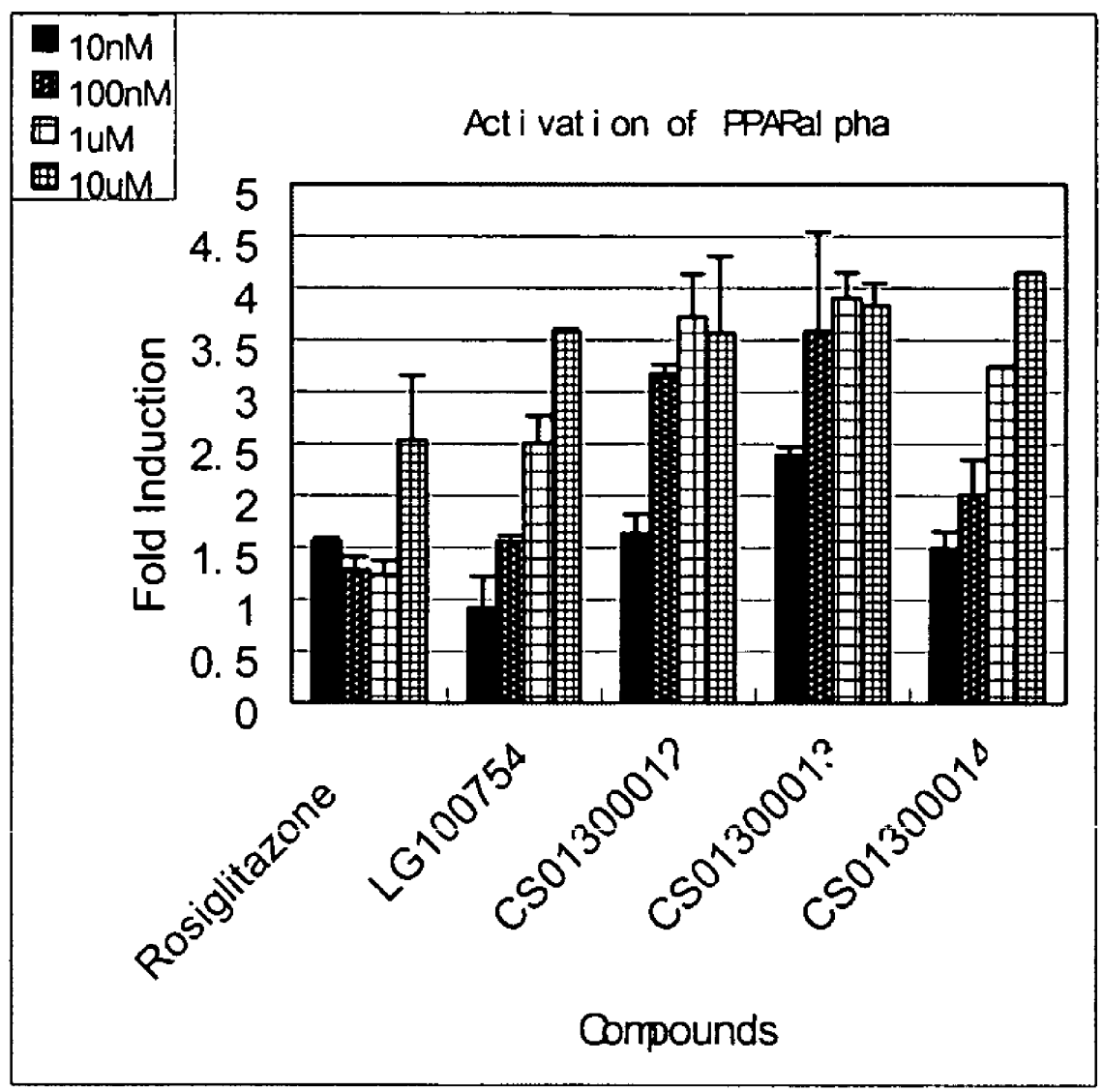
FIG. 1 graphically illustrates comparative activation of RXR/PPAR alpha heterodimers by compounds of the present invention (Example 30).

Unless defined otherwise, all technical and scientific terms used herein have the same meaning as is commonly understood by one of skill in the art to which this invention belongs. All publications and patents referred to herein are incorporated by reference.

As used in the above structural formula I and throughout the present specification, the following terms have the indicated meaning:

The term "alkyl" as used herein is intended to include those alkyl groups in either a linear or branched or cyclic configuration. Typical alkyl groups include, but are not limited to, methyl, ethyl, n-propyl, iso-propyl, butyl, iso-butyl, sec-butyl, tert-butyl, penyl, iso-pentyl, hexyl, iso-hexyl, cyclopropyl, cyclobutyl, cyclopentyl, cyclohexyl and the like.

The term "aralkyl" as used herein refers to a straight or branched saturated carbon chain containing from 1 to 6 carbons substituted with an aromatic carbohydride, such as benzyl, phenethyl, 3-phenylpropyl, 1-naphtylmethyl and the like.

The term "heteroaralkyl" as used herein refers to a strait or branched saturated carbon chain containing from 1 to 6 carbons substituted with a heteroaryl as defined herein, such as (2-furyl)methyl, (3-furyl)methyl, (2-pyridyl)methyl and the like.

The term "aminoalkyl" as used herein refers to an alkyl as defined herein whereto is attached an amino group, such as aminoethyl, 1-aminopropyl, 2-aminopropyl and the like.

The term "alkoxyalkyl" as used herein refers to an alkyl as defined herein whereto is attached an alkoxy as defined herein, such as methoxymethyl, ethoxymethyl, methoxyethyl, ethoxyethyl and the like.

The term "aryloxyalkyl" as used herein refers to an alkyl as defined herein whereto is attached an aryloxy as defined herein, such as phenoxymethyl, phenoxydodecyl, 1-naphthyloxyethyl and the like.

The term "aralkoxyalkyl" as used herein refers to an alkyl as defined herein whereto is attached an aralkoxy as defined herein, such as benzyloxymethyl, 3-phenylpropoxyethyl and the like.

The term "hydroxyalkyl" as used herein refers to an alkyl as defined herein whereto is attached a hydroxy group, such as hydroxyethyl, 1-hydroxypropyl, 2-hydroxypropyl and the like.

The term "thioalkyl" as used herein refers to an alkyl as defined herein whereto is attached a group of formula of —SR' wherein R' is H, alkyl or aryl, such as thiomethyl, methylthiomethyl, phenylthioethyl and the like.

The term "heterocyclyl" as used herein means a monovalent saturated or unsaturated group being monocyclic and containing one or more heteroatoms, such as pyrrolidine, pyrroline, pyrazoline, imidazolidine, imidazoline, piperidine, morpholine and the like.

The term "halogen" as used herein means fluorine, chlorine, bromine or iodine.

The term "alkoxy" as used herein is intended to include those alkyl groups in either a linear or branched or cyclic configuration linked through an ether oxygen having its free valence bond from the ether oxygen, such as methoxy, ethoxy, propoxy, butoxy, pentoxy, isopropoxy, sec-butoxy, cyclopropyloxy, cyclohexyloxy and the like.

The term "aryl" as used herein is intended to include aromatic rings optionally substituted with halogen, amino, hydroxy, alkyl or alkoxy, such as phenyl, naphthyl and the like.

The term "aryloxy" as used herein refers to phenoxy, 1-naphthyloxy, 2-naphthyloxy and the like.

The term "aralkoxy" as used herein refers to an alkyl as defined herein substituted with an aromatic carbohydride, such as benzyloxy, phenethoxy, 1-naphthylmethoxy and the like.

The term "heteroaryl" as used herein refers to a monovalent substituent comprising a 5–6 membered monocyclic aromatic system or a 9–10 membered bicyclic aromatic system containing one or more heteroatoms selected from nitrogen, oxygen and sulfur, such as furan, thiophene, pyrrole, imidazole, triazole, pyridine, pyrazine, pyrimidine, oxazole, quinoline, indole, benzimidazole and the like.

The term "heteroaryloxy" as used herein refers to a heteroaryl as defined herein linked to an oxygen atom having its free valence bond from the oxygen atom, such as pyrrole, imidazole, triazole, pyridine, pyrazine, pyrimidine, oxazole, quinoline, indole, benzimidazole linked to oxygen.

The term "heteroaralkoxy" as used herein refers to a heteroaralkyl as defined herein linked to an oxygen atom having its free valence bond from the oxygen atom, such as (2-furyl)methyl, (3-furyl)methyl, (2-pyridyl)methyl linked to oxygen.

The term "acyl" as used herein refers to a monovalent substituent comprising an alkyl group linked through a carbonyl group, such as acetyl, propionyl, butyryl, isobutyryl, pivaloyl, valeryl and the like.

The term "acyloxy" as used herein refers to an acyl as defined herein linked to an oxygen atom having its free valence bond from the oxygen atom, such as acetyloxy, propionyloxy, butyryloxy, isobutyryloxy, pivaloyloxy, valeryloxy and the like.

The term "alkylamino" as used herein refers to a straight or branched or cyclic monovalent substituent comprising an alkyl group linked through amino having a free valence bond from the nitrogen atom, such as methylamino, ethylamino, propylamino, butylamino, cyclopropylamino, cyclopentylamino, cyclohexylamino and the like.

The term "arylamino" as used herein refers to an aryl as defined herein linked through amino having a free valence bond from the nitrogen atom, such as phenylamino, naphthylamino and the like.

The term "aralkylamino" as used herein refers to an aralkyl as defined herein linked through amino having a free valence bond from the nitrogen atom, such as benzylamino, phenethylamino, 3-phenylpropylamino, 1-naphtylmethylamino and the like.

In a preferred embodiment, the compounds of this invention are those of the formula I, wherein
ring A is a 6-membered cyclic ring;
ring B is a 6-membered aromatic ring;
X and Y are independently O;
Z is O or NR$^7$ wherein R$^7$ represents hydrogen, alkyl, aryl, or arylalkyl;

Q is O or $NR^7$ wherein $R^7$ represents hydrogen, alkyl, aryl, or arylalkyl;

$R^1$, $R^2$ and $R^3$ are independently H or alkyl;

$R^4$ and $R^5$ are independently H or alkyl;

Ar is an arylene group;

n is 2.

In a preferred embodiment, the compounds of this invention are those of the formula I, wherein ring A is a 6-membered cyclic ring;

ring B is benzene ring;

X and Y are independently O;

Z is O or $NR^7$ wherein $R^7$ represents hydrogen;

Q is O or $NR^7$ wherein $R^7$ represents hydrogen;

$R^1$, $R^2$ and $R^3$ are independently H;

$R^4$ and $R^5$ are independently H or methyl;

Ar is benzene group;

n is 2;

The compounds of formula I and the novel synthetic intermediates of formula II can be prepared by the synthetic route shown in Scheme 1:

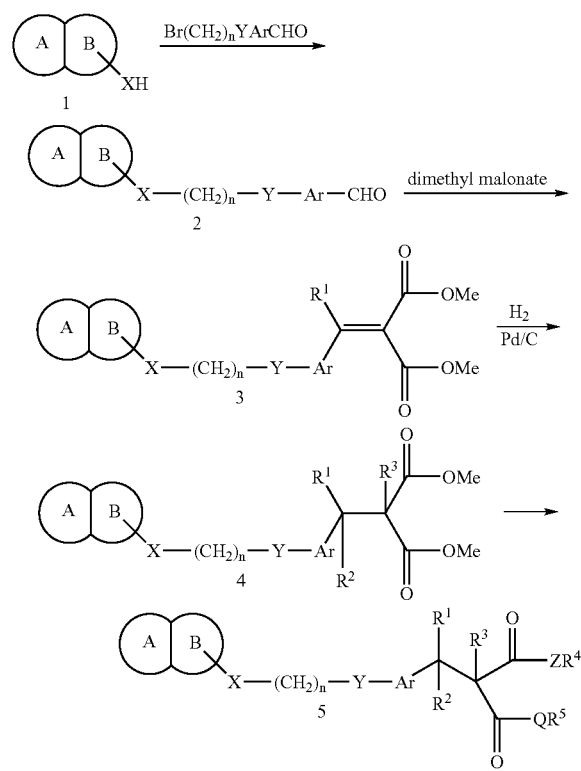

The reaction of compound 1 with p-bromoethoxy benzaldehyde produced benzaldehyde derivative 2 in 40–45% yield. Knoevenagel condensation between the aldehyde 2 and dimethyl malonate gave the benzylidene 3 in 92–98% yield. Catalytic hydrogenation of 3 with 5% palladium on carbon gave the dimethyl malonate 4. Partial hydrolysis of 4 with 1 equiv of sodium hydroxide gave the half-ester 5a (Z=O, Q=O, $R^4$=H, $R^5$=$CH_3$) in 90–95% yield. Hydrolysis of 4 with more than 2 equiv of sodium hydroxide gave the malonic acid 5b (Z=O, Q=O, $R^4$=H, $R^1$=H) in 94–98% yield. The Schotten-Baumann reaction between an acid chloride of 5a and ammonia gave the amide ester 5c (Z=NH, Q=O, $R^4$=H, $R^5$=$CH_3$) in 52–58% yield. The amide acid 5d (Z=NH, Q=O, $R^4$=H, $R^5$=H) was prepared by hydrolysis of 5c in 65–69% yield.

The pharmaceutical composition of the present invention can be in any form, such as tablets, capsules, powders, syrups, solutions, suspensions, aerosols, and the like. It can also include flavors, sweeteners etc. in suitable solids or liquid carriers or diluents, or in suitable sterile media to form injectable solutions or suspensions. In a preferred embodiment, the pharmaceutical composition contains up to about 65% of the compounds of formula I by weight, preferably from about 0.5 to about 40%, more preferably from about 1 to about 20%, and most preferably from about 1 to 10% with the remainder of the composition being pharmaceutically acceptable carriers, diluents or solvents or salt solutions.

As used herein, the term "pharmaceutically acceptable carrier" or "diluent" includes, but is not limited to those disclosed in "Handbook of Pharmaceutical Excipients" published in October, 1986 by American Pharmaceutical Association, the content of which is incorporated herein by reference to the extent permitted.

The compounds of the formula I as defined above are clinically administered to mammals, including humans and animals, via oral, nasal, transdermal, pulmonary, or parenteral routes. Administration by the oral route is preferred, being more convenient and avoiding the possible pain and irritation of injection. In a preferred embodiment, the dosage is in the range from about 0.01 to about 200 mg/kg body weight per day, administered singly or as a divided dose, preferably from about 0.01 to about 100 mg/kg and more preferably from about 0.1 to about 50 mg/kg. However, the optimal dosage for the individual subject being treated will be determined by the person responsible for treatment, generally a smaller dose is administered initially and increments are made thereafter to determine the most suitable dosage.

Without intending to be bound by any particular theory of operation, it is believed that the administration of compounds of formula I to a patient treats diabetes and complications associated with it by lowering the patient's glucose and triglyceride levels. Such dual activities, for example, would help the patient to circumvent hyperglycemia and hypertriglyceremia associated with type 2 diabetes.

The following examples are given as specific illustrations of the invention. It should be understood, however, that the invention is not limited to the specific details set forth in the examples. All parts and percentages in the examples, as well as in the remainder of the specification, are by weight unless otherwise specified.

Further, any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result.

EXAMPLE 1

Preparation of 2,5-dichloro-2,5-dimethylhexane

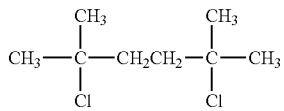

Thionyl chloride (25 ml, 341.8 mmol) is added at ambient temperature to a solution of 2,5-dimethyl-2,5-hexanediol (20.0 g, 136.8 mmol) in 250 ml of dichloromethane. The reaction mixture is stirred for 4 hours. Then 250 ml of distilled water is added. The organic phase is separated and washed with 10% NaHCO$_3$ solution (2×250 ml), then dried over MgSO$_4$ and evaporated to dryness to give the title compound (18.37 g, 73%).

$^1$H NMR (CDCl$_3$): 1.57 (s, 12H, CH$_3$); 1.92 (s, 4H, CH$_2$).

EXAMPLE 2

Preparation of 5,5,8,8-tetramethyl-5,6,7,8-tetrahydro-2-naphthol

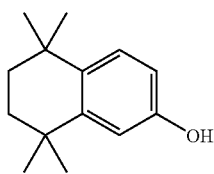

To a mixture of aluminum trichloride (3.0 g, 22.5 mmol), dichloromethane (50 ml) and 2,5-dichloro-2,5-dimethylhexane (15.0 g, 81.9 mmol) is added dropwise into a solution of phenol (7.7 g, 81.90 mmol) in 50 ml of methane dichloride, then the reaction mixture is heated for 4 hours at 35° C. After cooled, the reaction mixture is poured into ice (200 g) and extracted with ether (3×80 ml). The organic phase is washed with 10% NaHCO$_3$ solution (2×150 ml), dried over MgSO$_4$ and evaporated to give a crude product, which is crystallized from ethanol to give the title compound (15.20 g, 84%).

EXAMPLE 3

Preparation of 4-(2-bromoethoxy)benzaldehyde

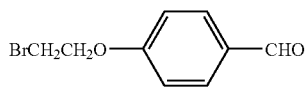

To a solution of potassium hydroxide (3.70 g, 54.0 mmol) in ethanol (50 ml) is added 4-hydroxybenzaldehyde (6.00 g, 49.1 mmol) and 1,2-dibromoethane (46.15 g, 245.7 mmol). Then the mixture is heated to reflux for 8 hours. After cooled, the reaction mixture is evaporated under vacuum. The residue is dissolved in water and extracted with dichloromethane (3×50 ml). The organic phase is washed with water (3×50 ml), dried over MgSO$_4$ and evaporated to give a crude product, which is crystallized from ethanol to give the title compound (4.60 g, 41%).

EXAMPLE 4

Preparation of 4-[2-(5,5,8,8-tetramethyl-5,6,7,8-tetrahydro-2-naphthoxy)ethoxy]benzaldehyde

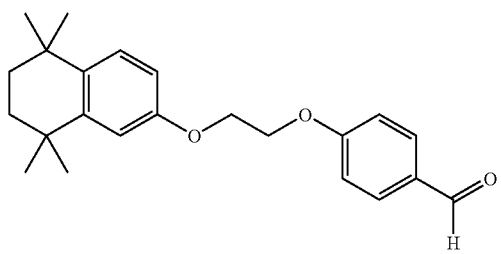

To a solution of potassium hydroxide (0.67 g, 9.80 mmol) in ethanol (30 ml) is added 5,5,8,8-tetramethyl-5,6,7,8-tetrahydro-2-naphthol (2.00 g, 9.80 mmol) and 4-(2-bromoethoxy)benzaldehy (2.25 g, 9.80 mmol). Then the mixture is heated to reflux for 8 hours. After cooled to −5° C., the precipitate is collected by filtration, washed with water, and dried under vacuum to give the title product (1.60 g, 46.4%).

EXAMPLE 5

Preparation of dimethyl 4-[2-(5,5,8,8-tetramethyl-5,6,7,8-tetrahydro-2-naphthoxy)ethoxy]benzylidenemalonate

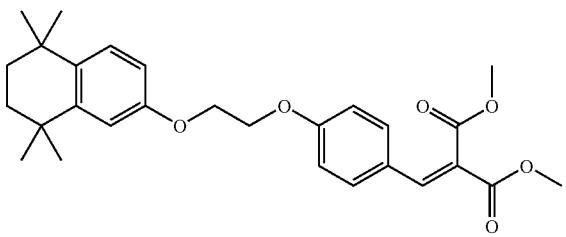

To a solution of 4-[2-(5,5,8,8-tetramethyl-5,6,7,8-tetrahydro-2-naphthoxy)ethoxy]benzaldehyde (1.50 g, 4.26 mmol) and dimethyl malonate (1.69 g, 12.78 mmol) in toluene (30 ml) is added a catalytic quantity of piperidinium acetate. Then the mixture is refluxed in a Dean-Stark trap for 8 hours. After cooled to room temperature, the solution is concentrated under a vacuum to give title compound (1.95 g, 98%).

EXAMPLE 6

Preparation of dimethyl 4-[2-(5,5,8,8-tetramethyl-5,6,7,8-tetrahydro-2-naphthoxy)ethoxy]benzylmalonate

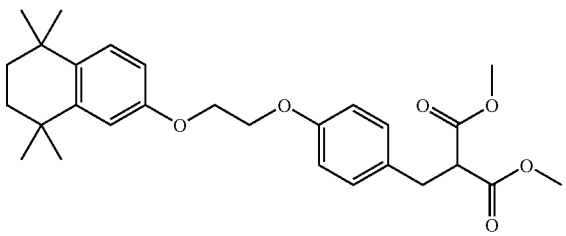

To a solution of dimethyl 4-[2-(5,5,8,8-tetramethyl-5,6,7,8-tetrahydro-2-naphthoxy)ethoxy]benzylidenemalonate (2.55 g, 5.47 mmol) in a mixture of methanol (20 ml) and 1,4-dioxane (150 ml) is added 5% palladium on charcoal (1.20 g). Then the mixture is stirred under an atmosphere of hydrogen at room temperature until hydrogen uptake ceased. The solution is filtered through Celite, and the filtrate is evaporated under a vacuum. The residue is crystallized from ethyl acetate to give the title compound (2.45 g, 96%). HRMS calcd for $C_{28}H_{36}O_6$: 468.5902. Found: 468.5905. MA calcd for $C_{28}H_{36}O_6$: C, 71.77%; H, 7.74%. Found: C, 71.52%; H, 7.76%.

EXAMPLE 7

Preparation of 2-(methoxycarbonyl)-3-[4-[2-(5,5,8,8-tetramethyl-5,6,7,8-tetrahydro-2-naphthoxy)ethoxy]phenyl]propionic acid

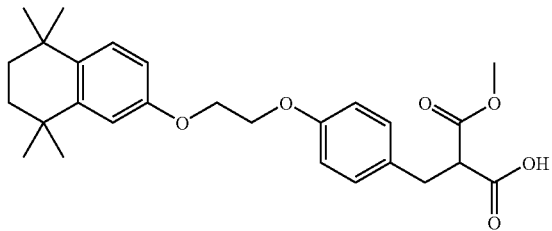

To a solution of dimethyl 4-[2-(5,5,8,8-tetramethyl-5,6,7,8-tetrahydro-2-naphthoxy)ethoxy]benzylmalonate (0.50 g, 1.07 mmol) in a mixture of methanol (4.3 ml) and tetrahydrofuran (2.1 ml) at 0° C. is added a 2 mol/L aqueous solution of sodium hydroxide (0.59 ml, 1.18 mmol). The mixture is stirred for 2 hours at room temperature, and then the solvent was removed under a vacuum. The residue is dissolved in saturated aqueous sodium bicarbonate (10 ml) and washed with ethyl acetate (10 ml). The aqueous solution is acidified to pH 2–3 with dilute hydrochloric acid and extracted with ethyl acetate (3×15 ml). The combined extracts are washed with water (20 ml) and brine (20 ml), dried over sodium sulfate, and concentrated. The residue is crystallized from ethyl acetate to give the title compound (0.45 g, 93%). HRMS calcd for $C_{27}H_{34}O_6$: 454.5634. Found: 454.5636. MA calcd for $C_{27}H_{34}O_6$: C, 71.34%; H, 7.54%. Found: C, 71.42%; H, 7.52%.

EXAMPLE 8

Preparation of 2-[4-[2-(5,5,8,8-tetramethyl-5,6,7,8-tetrahydro-2-naphthoxy)ethoxy]benzyl]malonic acid

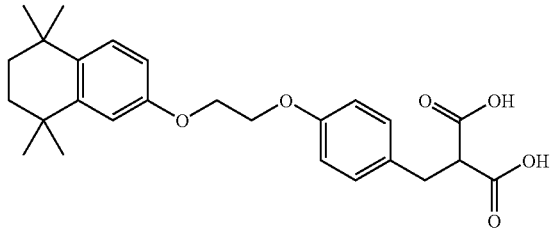

To a solution of dimethyl 4-[2-(5,5,8,8-tetramethyl-5,6,7,8-tetrahydro-2-naphthoxy)ethoxy]benzylmalonate (1.50 g, 3.21 mmol) in a mixture of methanol (12.9 ml) and tetrahydrofuran (6.4 ml) is added a 2 mol/L aqueous solution of sodium hydroxide (8.01 ml, 16.03 mmol). The mixture is stirred for 2 hours at room temperature, and then the solvent was removed under a vacuum. The residue is dissolved in water and washed with ethyl acetate (10 ml). The aqueous solution is acidified to pH 2–3 with dilute hydrochloric acid and extracted with ethyl acetate (3×15 ml). The combined extracts are washed with water (20 ml) and brine (20 ml), dried over sodium sulfate, and concentrated. The residue is crystallized from ethyl acetate to give the title compound (1.38 g, 98%). HRMS calcd for $C_{26}H_{32}O_6$: 440.5365. Found: 440.5363. MA calcd for $C_{26}H_{32}O_6$: C, 70.89%; H, 7.32%. Found: C, 70.72%; H, 7.36%.

EXAMPLE 9

Preparation of methyl 2-carbamoyl-3-[4-[2-(5,5,8,8-tetramethyl-5,6,7,8-tetrahydro-2-naphthoxy)ethoxy]phenyl]propionate

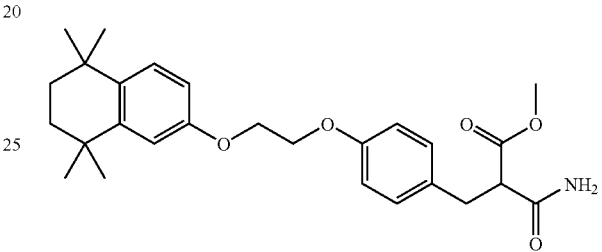

To a solution of 2-(methoxycarbonyl)-3-[4-[2-(5,5,8,8-tetramethyl-5,6,7,8-tetrahydro-2-naphthoxy)ethoxy]phenyl]propionic acid (2.40 g, 5.29 mmol) in benzene (20 ml) at room temperature is added thionyl chloride (0.76 g, 6.34 mmol). Then the mixture is heated at 80° C. for 90 min. After cooled to room temperature, the solvent is removed under a vacuum. To the residue is added 28% ammonia solution (5.49 ml, 79.30 mmol) at room temperature. The mixture is stirred for 30 min, dissolved in ethyl acetate (20 ml), washed with brine (3×15 ml), dried over sodium sulfate, and concentrated. The crude product is crystallized from ethanol to give title compound (1.35 g, 56%). HRMS calcd for $C_{27}H_{35}NO_5$: 453.5786. Found: 453.5784. MA calcd for $C_{27}H_{35}NO_5$: C, 71.50%; H, 7.78%; N, 3.09. Found: C, 71.52%; H, 7.76%; N, 3.12%.

EXAMPLE 10

Preparation of 2-carbamoyl-3-[4-[2-(5,5,8,8-tetramethyl-5,6,7,8-tetrahydro-2-naphthoxy)ethoxy phenyl]propionic acid

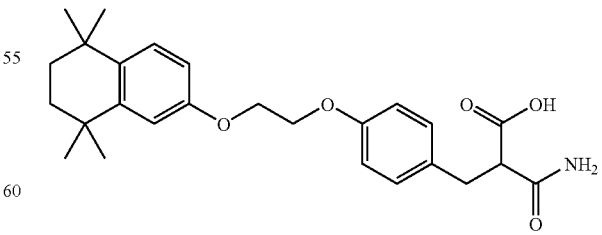

To a solution of methyl 2-cabamoyl-3-[4-[2-(5,5,8,8-tetramethyl-5,6,7,8-tetrahydro-2-naphthoxy)ethoxy]phenyl] propionate (0.50 g, 1.10 mmol) in methanol (5 ml) and tetrahydrofuran (5 ml) at room temperature is added a 2.5 mol/L solution of aqueous sodium hydroxide (0.44 ml, 1.10 mmol). The mixture is stirred for 15 hours at room temperature, and then the solvent is removed under a vacuum. The residue is dissolved in water (20 ml), acidified to pH 1–2 with 3 mol/L hydrochloric acid, and the precipitate is collected by filtration. The crude product is washed with water and crystallized from methanol to give title compound (0.35 g, 68%). HRMS calcd for $C_{26}H_{33}NO_5$: 439.5518. Found: 439.5516. MA calcd for $C_{26}H_{33}NO_5$: C, 71.05%; H, 7.57%; N, 3.19. Found: C, 71.08%; H, 7.60%; N, 3.16%.

EXAMPLE 11

Preparation of 4-[2-(5,6,7,8,-tetrahydro-2-naphthoxy)ethoxy]benzaldehyde

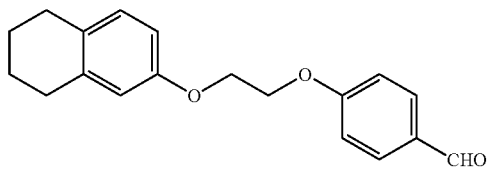

To a solution of potassium hydroxide (0.67 g, 9.80 mmol) in ethanol (30 ml) is added 5,6,7,8-tetrahydro-2-naphthol (1.45 g, 9.80 mmol) and 4-(2-bromoethoxy)benzaldehyde (2.25 g, 9.80 mmol). Then the mixture is heated to reflux for 8 hours. After cooled to −5° C., the precipitate is collected by filtration, washed with water, and dried under vacuum to give the title product (1.39 g, 48.0%).

EXAMPLE 12

Preparation of dimethyl 4-[2-(5,6,7,8-tetrahydro-2-naphthoxy)ethoxy]benzylidenemalonate

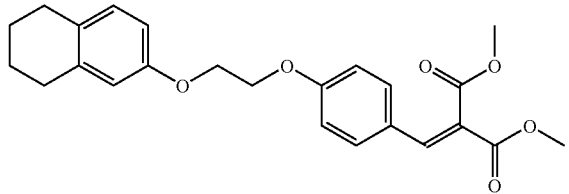

To a solution of 4-[2-(5,6,7,8,-tetrahydro-2-naphthoxy)ethoxy]benzaldehyde (1.26 g, 4.26 mmol) and dimethyl malonate (1.69 g, 12.78 mmol) in toluene (30 ml) is added a catalytic quantity of piperidinium acetate. Then the mixture is refluxed in a Dean-Stark trap for 8 hours. After cooled to room temperature, the solution was concentrated under a vacuum to give title compound (1.68 g, 96%).

EXAMPLE 13

Preparation of dimethyl 4-[2-(5,6,7,8-tetrahydro-2-naphthoxy)ethoxy]benzylmalonate

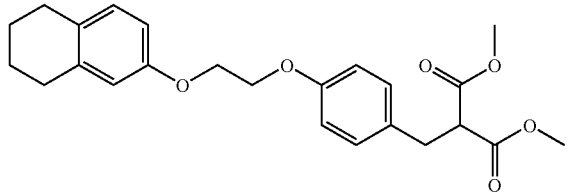

To a solution of dimethyl 4-[2-(5,6,7,8-tetrahydro-2-naphthoxy)ethoxy]benzylidenemalonate (2.24 g, 5.47 mmol) in a mixture of methanol (20 ml) and 1,4-dioxane (150 ml) is added 5% palladium on charcoal (1.20 g). Then the mixture is stirred under an atmosphere of hydrogen at room temperature until hydrogen uptake ceased. The solution is filtered through Celite, and the filtrate is evaporated under a vacuum. The residue is crystallized from ethyl acetate to give the title compound (2.16 g, 96%). HRMS calcd for $C_{24}H_{28}O_6$: 412.4827. Found: 412.4825. MA calcd for $C_{24}H_{28}O_6$: C, 69.99%; H, 6.84%. Found: C, 69.82%; H, 6.88%.

EXAMPLE 14

Preparation of 2-(methoxycarbonyl)-3-[4-[2-(5,6,7,8-tetrahydro-2-naphthoxy)ethoxy]phenyl]propionic acid

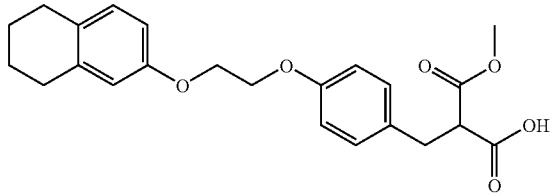

To a solution of dimethyl 4-[2-(5,6,7,8-tetrahydro-2-naphthoxy)ethoxy]benzylmalonate (0.44 g, 1.07 mmol) in a mixture of methanol (4.3 ml) and tetrahydrofuran (2.1 ml) at 0° C. is added a 2 mol/L aqueous solution of sodium hydroxide (0.59 ml, 1.18 mmol). The mixture is stirred for 2 h at room temperature, and then the solvent is removed under a vacuum. The residue was dissolved in saturated aqueous sodium bicarbonate (10 ml) and washed with ethyl acetate (10 ml). The aqueous solution is acidified to pH 2–3 with dilute hydrochloric acid and extracted with ethyl acetate (3×15 ml). The combined extracts are washed with water (20 ml) and brine (20 ml), dried over sodium sulfate, and concentrated. The residue is crystallized from ethyl acetate to give the title compound (0.38 g, 90%). HRMS calcd for $C_{23}H_{26}O_6$: 398.4558. Found: 398.4556. MA calcd for $C_{23}H_{26}O_6$: C, 69.33%; H, 6.58%. Found: C, 69.32%; H, 6.59%.

EXAMPLE 15

Preparation of 2-[4-[2-(5,6,7,8-tetrahydro-2-naphthoxy)ethoxy]benzyl]malonic acid

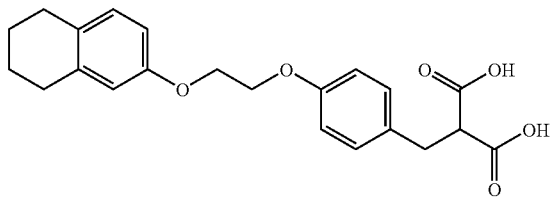

To a solution of dimethyl 4-[2-(5,6,7,8-tetrahydro-2-naphthoxy)ethoxy]benzylmalonate (1.28 g, 3.21 mmol) in a mixture of methanol (12.9 ml) and tetrahydrofuran (6.4 ml)

is added a 2 mol/L aqueous solution of sodium hydroxide (8.01 ml, 16.03 mmol). The mixture is stirred for 2 hours at room temperature, and then the solvent was removed under a vacuum. The residue is dissolved in water and washed with ethyl acetate (10 ml). The aqueous solution is acidified to pH 2–3 with dilute hydrochloric acid and extracted with ethyl acetate (3×15 ml). The combined extracts are washed with water (20 ml) and brine (20 ml), dried over sodium sulfate, and concentrated. The residue is crystallized from ethyl acetate to give the title compound (1.17 g, 95%). HRMS calcd for $C_{22}H_{24}O_6$: 384.4290. Found: 384.4291. MA calcd for $C_{22}H_{24}O_6$: C, 68.74%; H, 6.29%. Found: C, 68.69%; H, 6.31%.

EXAMPLE 16

Preparation of methyl 2-carbamoyl-3-[4-[2-(5,6,7,8-tetrahydro-2-naphthoxy)ethoxy]phenyl]propionate

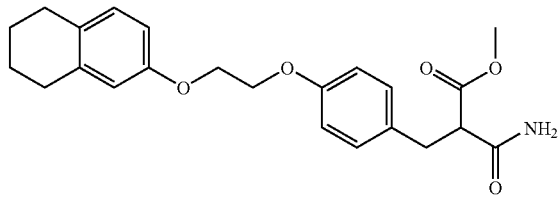

To a solution of 2-(methoxycarbonyl)-3-[4-[2-(5,6,7,8-tetrahydro-2-naphthoxy)ethoxy]phenyl]propionic acid (2.10 g, 5.29 mmol) in benzene (20 ml) at room temperature is added thionyl chloride (0.76 g, 6.34 mmol). Then the mixture was heated at 80° C. for 90 min. After cooled to rooms temperature, the solvent is removed under a vacuum. To the residue is added 28% ammonia solution (5.49 ml, 79.30 mmol) at room temperature. The mixture is stirred for 30 min, dissolved in ethyl acetate (20 ml), washed with brine (3×15 ml), dried over sodium sulfate, and concentrated. The crude product is crystallized from ethanol to give title compound (1.09 g, 52%). HRMS calcd for $C_{23}H_{27}NO_5$: 397.4711. Found: 397.4713. MA calcd for $C_{23}H_{27}NO_5$: C, 69.50%; H, 6.85%; N, 3.52%. Found: C, 69.62%; H, 6.83%; N, 3.53%.

EXAMPLE 17

Preparation of 2-carbamoyl-3-[4-[2-(5,6,7,8-tetrahydro-2-naphthoxy)ethoxy]phenyl]propionic acid

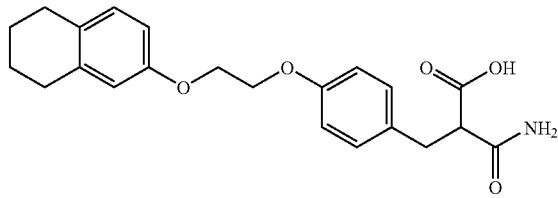

To a solution of methyl 2-cabamoyl-3-[4-[2-(5,6,7,8-tetrahydro-2-naphthoxy)ethoxy]phenyl]propionate (0.44 g, 1.10 mmol) in methanol (5 ml) and tetrahydrofuran (5 ml) at room temperature is added a 2.5 mol/L solution of aqueous sodium hydroxide (0.44 ml, 1.10 mmol). The mixture is stirred for 15 hours at room temperature, and then the solvent is removed under a vacuum. The residue is dissolved in water (20 ml), acidified to pH 1–2 with 3 mol/L hydrochloric acid, and the precipitate is collected by filtration. The crude product is washed with water and crystallized from methanol to give title compound (0.28 g, 66%). HRMS calcd for $C_{22}H_{25}NO_5$: 383.4442. Found: 383.4444. MA calcd for $C_{22}H_{25}NO_5$: C, 68.91%; H, 6.57%; N, 3.65%. Found: C, 68.82%; H, 6.55%; N, 3.67%.

EXAMPLE 18

Preparation of 4-[2-(2-naphthoxy)ethoxy]benzaldehyde

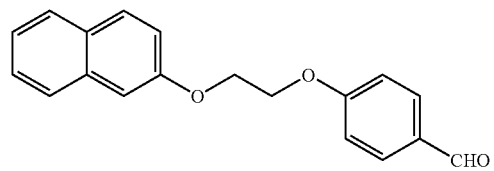

To a solution of potassium hydroxide (0.67 g, 9.80 mmol) in ethanol (30 ml) is added 2-naphthol (1.41 g, 9.80 mmol) and 4-(2-bromoethoxy)benzaldehyde (2.25 g, 9.80 mmol). Then the mixture is heated to reflux for 8 hours. After cooled to −5° C., the precipitate is collected by filtration, washed with water, and dried under vacuum to give the title product (1.03 g, 36%).

EXAMPLE 19

Preparation of dimethyl 4-[2-(2-naphthoxy)ethoxy]benzylidenemalonate

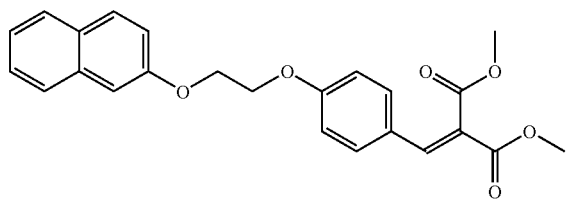

To a solution of 4-[2-(2-naphthoxy)ethoxy]benzaldehyde (1.24 g, 4.26 mmol) and dimethyl malonate (1.69 g, 12.78 mmol) in toluene (30 ml) is added a catalytic quantity of piperidinium acetate. Then the mixture is refluxed in a Dean-Stark trap for 8 hours. After cooled to room temperature, the solution was concentrated under a vacuum to give title compound (1.45 g, 84%).

EXAMPLE 20

Preparation of dimethyl 4-[2-(2-naphthoxy)ethoxy]benzylmalonate (Lab Code CS01200204)

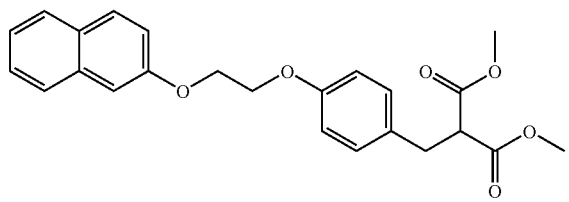

To a solution of dimethyl 4-[2-(2-naphthoxy)ethoxy]benzylidenemalonate (2.22 g, 5.47 mmol) in a mixture of methanol (20 ml) and 1,4-dioxane (150 ml) is added 5% palladium on charcoal (1.20 g). Then the mixture is stirred under an atmosphere of hydrogen at room temperature until hydrogen uptake ceased. The solution is filtered through Celite, and the filtrate is evaporated under a vacuum. The residue is crystallized from ethyl acetate to give the title compound (2.10 g, 94%). HRMS calcd for $C_{24}H_{24}O_6$: 408.4476. Found: 408.4475. MA calcd for $C_{24}H_{24}O_6$: C, 70.58%; H, 5.92%. Found: C, 70.71%; H, 5.89%.

EXAMPLE 21

Preparation of 2-(methoxycarbonyl)-3-[4-[2-(2-naphthoxy)ethoxy]phenyl]propionic acid (Lab Code CS01200205)

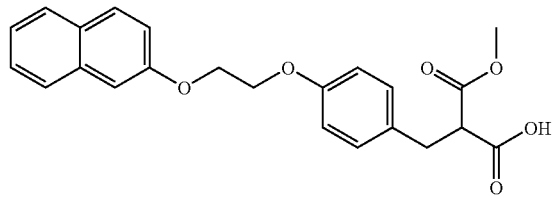

To a solution of dimethyl 4-[2-(2-naphthoxy)ethoxy]benzylmalonate (0.44 g, 1.07 mmol) in a mixture of methanol (4.3 ml) and tetrahydrofuran (2.1 ml) at 0° C. is added a 2 mol/L aqueous solution of sodium hydroxide (0.59 ml, 1.18 mmol). The mixture is stirred for 2 h at room temperature, and then the solvent is removed under a vacuum. The residue was dissolved in saturated aqueous sodium bicarbonate (10 ml) and washed with ethyl acetate (10 ml). The aqueous solution is acidified to pH 2–3 with dilute hydrochloric acid and extracted with ethyl acetate (3×15 ml). The combined extracts are washed with water (20 ml) and brine (20 ml), dried over sodium sulfate, and concentrated. The residue is crystallized from ethyl acetate to give the title compound (0.35 g, 83%). HRMS calcd for $C_{23}H_{22}O_6$: 394.4208. Found: 394.4206. MA calcd for $C_{23}H_{22}O_6$: C, 70.04%; H, 5.62%. Found: C, 70.18%; H, 5.66%.

EXAMPLE 22

Preparation of methyl 2-carbamoyl-3-[4-[2-(2-naphthoxy)ethoxy]phenyl]propionate

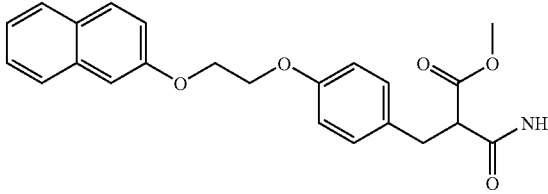

To a solution of 2-(methoxycarbonyl)-3-[4-[2-(2-naphthoxy)ethoxy]phenyl]propionic acid (2.08 g, 5.29 mmol) in benzene (20 ml) at room temperature is added thionyl chloride (0.76 g, 6.34 mmol). Then the mixture was heated at 80° C. for 90 min. After cooled to room temperature, the solvent is removed under a vacuum. To the residue is added 28% ammonia solution (5.49 ml, 79.30 mmol) at room temperature. The mixture is stirred for 30 min, dissolved in ethyl acetate (20 ml), washed with brine (3×15 ml), dried over sodium sulfate, and concentrated. The crude product is crystallized from ethanol to give title compound (0.98 g, 47%). HRMS calcd for $C_{23}H_{23}NO_5$: 393.4364. Found: 393.4363. MA calcd for $C_{23}H_{23}NO_5$: C, 70.22%; H, 5.89%; N, 3.56%. Found: C, 70.54%; H, 5.87%; N, 3.54%.

EXAMPLE 23

Preparation of 2-carbamoyl-3-[4-[2-(2-naphthoxy)ethoxy]phenyl]propionic acid (Lab Code CS01200207)

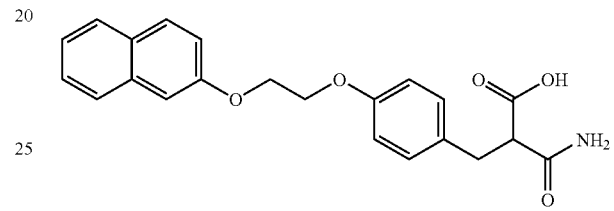

To a solution of methyl 2-cabamoyl-3-[4-[2-(2-naphthoxy)ethoxy]phenyl]propionate (0.43 g, 1.10 mmol) in methanol (5 ml) and tetrahydrofuran (5 ml) at room temperature is added a 2.5 mol/L solution of aqueous sodium hydroxide (0.44 ml, 1.10 mmol). The mixture is stirred for 15 hours at room temperature, and then the solvent is removed under a vacuum. The residue is dissolved in water (20 ml), acidified to pH 1–2 with 3 mol/L hydrochloric acid, and the precipitate is collected by filtration. The crude product is washed with water and crystallized from methanol to give title compound (0.24 g, 58%). HRMS calcd for $C_{22}H_{21}NO_5$: 379.4096. Found: 379.4098. MA calcd for $C_{22}H_{21}NO_5$: C, 69.64%; H, 5.58 3.69%. Found: C, 69.48%; H, 5.55%; N, 3.70%.

EXAMPLE 24

Preparation of 4-[2-(6-quinolinoxy)ethoxy]benzaldehyde

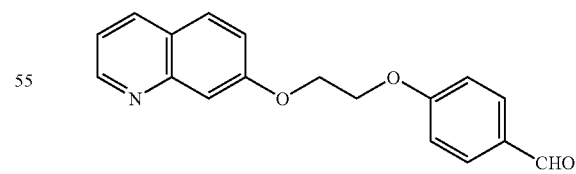

To a solution of potassium hydroxide (0.67 g, 9.80 mmol) in ethanol (30 ml) is added 6-quinolinol (1.42 g, 9.80 mmol) and 4-(2-bromoethoxy)benzaldehyde (2.25 g, 9.80 mmol). Then the mixture is heated to reflux for 8 hours. After cooled to −5° C., the precipitate is collected by filtration, washed with water, and dried under vacuum to give the title product (1.26 g, 44%).

EXAMPLE 25

Preparation of dimethyl 4-[2-(6-quinolinoxy)ethoxy]benzylidenemalonate

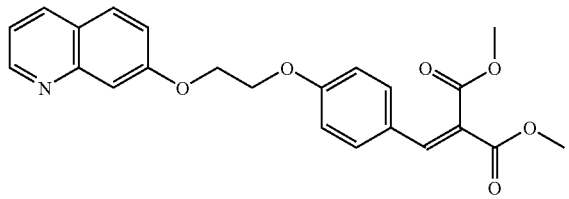

To a solution of 4-[2-(6-quinolinoxy)ethoxy]benzaldehyde (1.25 g, 4.26 mmol) and dimethyl malonate (1.69 g, 12.78 mmol) in toluene (30 ml) is added a catalytic quantity of piperidinium acetate. Then the mixture is refluxed in a Dean-Stark trap for 8 hours. After cooled to room temperature, the solution was concentrated under a vacuum to give title compound (1.51 g, 87%).

EXAMPLE 26

Preparation of dimethyl 4-[2-(6-quinolinoxy)ethoxy]benzylmalonate (Lab Code CS01200304)

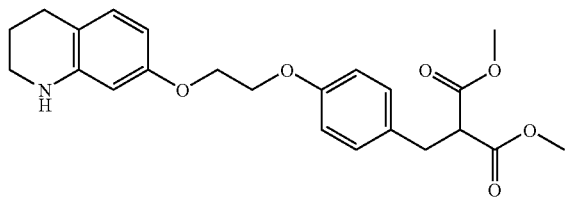

To a solution of dimethyl 4-[2-(6-quinolinoxy)ethoxy]benzylidenemalonate (2.23 g, 5.47 mmol) in a mixture of methanol (20 ml) and 1,4-dioxane (150 ml) is added 5% palladium on charcoal (1.20 g). Then the mixture is stirred under an atmosphere of hydrogen at room temperature until hydrogen uptake ceased. The solution is filtered through Celite, and the filtrate is evaporated under a vacuum. The residue is crystallized from ethyl acetate to give the title compound (2.04 g, 90%). HRMS calcd for $C_{23}H_{27}NO_6$: 413.4670. Found: 413.4672. MA calcd for $C_{23}H_{27}NO_6$: C, 66.81%; H, 6.58%; N, 3.39%. Found: C, 66.53%; H, 6.55%; N, 3.36%.

EXAMPLE 27

Preparation of 2-(methoxycarbonyl)-3-[4-[2-(6-quinolinoxy)ethoxy]phenyl]propionic acid (Lab Code CS01200305)

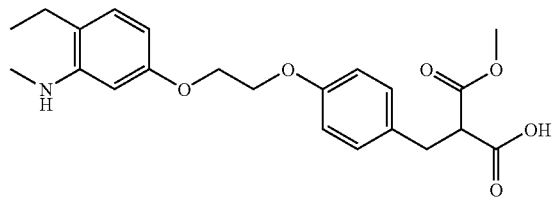

To a solution of dimethyl 4-[2-(6-quinolinoxy)ethoxy]benzylmalonate (0.44 g, 1.07 mmol) in a mixture of methanol (4.3 ml) and tetrahydrofuran (2.1 ml) at 0° C. is added a 2 mol/L aqueous solution of sodium hydroxide (0.59 ml, 1.18 mmol). The mixture is stirred for 2 h at room temperature, and then the solvent is removed under a vacuum. The residue was dissolved in saturated aqueous sodium bicarbonate (10 ml) and washed with ethyl acetate (10 ml). The aqueous solution is acidified to pH 2–3 with dilute hydrochloric acid and extracted with ethyl acetate (3×15 ml). The combined extracts are washed with water (20 ml) and brine (20 ml), dried over sodium sulfate, and concentrated. The residue is crystallized from ethyl acetate to give the title compound (0.23 g, 54%). HRMS calcd for $C_{22}H_{25}NO_6$: 399.4402. Found: 399.4405. MA calcd for $C_{22}H_{25}NO_6$: C, 66.15%; H, 6.31%; N, 3.51%. Found: C, 66.32%; H, 6.34%; N, 3.48%.

EXAMPLE 28

Preparation of methyl 2-carbamoyl-3-[4-[2-(6-quinolinoxy)ethoxy]phenyl]propionate

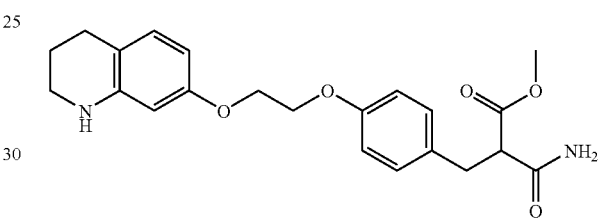

To a solution of 2-(methoxycarbonyl)-3-[4-[2-(6-quinolinoxy)ethoxy]phenyl]propionic acid (2.11 g, 5.29 mmol) in benzene (20 ml) at room temperature is added thionyl chloride (0.76 g, 6.34 mmol). Then the mixture was heated at 80° C. for 90 min. After cooled to room temperature, the solvent is removed under a vacuum. To the residue is added 28% ammonia solution (5.49 ml, 79.30 mmol) at room temperature. The mixture is stirred for 30 min, dissolved in ethyl acetate (20 ml), washed with brine (3×15 ml), dried over sodium sulfate, and concentrated. The crude product is crystallized from ethanol to give title compound (1.20 g, 57%). HRMS calcd for $C_{22}H_{26}N_2O_5$: 398.4558. Found: 398.4554. MA calcd for $C_{22}H_{26}N_2O_5$: C, 66.32%; H, 6.58%; N, 7.03%. Found: C, 66.44%; H, 6.54%; N, 7.05%

EXAMPLE 29

Preparation of 2-carbamoyl-3-[4-[2-(6-quinolinoxy)ethoxy]phenyl]propionic acid (Lab Code CS01200307)

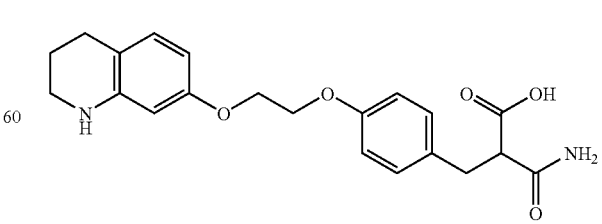

To a solution of methyl 2-cabamoyl-3-[4-[2-(6-quinolinoxy)ethoxy]phenyl]propionate (0.44 g, 1.10 mmol) in methanol (5 ml) and tetrahydrofuran (5 ml) at room temperature is added a 2.5 mol/L solution of aqueous sodium hydroxide (0.44 ml, 1.10 mmol). The mixture is stirred for 15 hours at room temperature, and then the solvent is removed under a vacuum. The residue is dissolved in water (20 ml), acidified to pH 1–2 with 3 mol/L hydrochloric acid, and the precipitate is collected by filtration. The crude product is washed with water and crystallized from methanol to give title compound (0.18 g, 43%). HRMS calcd for $C_{21}H_{24}N_2O_5$: 379.4096. Found: 379.4098. MA calcd for $C_{21}H_{24}N_2O_5$: C, 65.61N, 7.29%. Found: C, 65.44%; H, 6.27%; N, 7.33%.

EXAMPLE 30

Testing of dimethyl 4-[2-(5,6,7,8-tetrahydro-2-naphthoxy)ethoxy benzylmalonate (compounds CS0130012), 2-(methoxycarbonyl)-3-[4-[2-(5,6,7,8-tetrahydro-2-naphthoxy)ethoxy]phenyl]propionic acid (compound CS01300013) and 2-[4-[2-(5,6,7,8-tetrahydro-2-naphthoxy)ethoxy]benzyl]malonic acid (compound CS01300014) as an RXR/PPARalpha heterodimer agonist in vitro. See, FIG. 1.

Activation of RXR/PPARalpha heterodimer by indicated compounds was measured by luciferase reporter assay. Briefly, full length PPARalpha was cloned by PCR using oligonucleotide primers (5'-acgtgcttcctgcttcataga-3' (SEQ ID NO:1) and 5'-cctgagattagccacctccc-3' (SEQ ID NO:2)) from adipose tissue. The amplified cDNA was cloned into an expression vector and sequenced. The reporter was constructed by insertion of an annealed oligonucleotide containing three copies of the PPAR response element (5'-gatcctctcctttgacctattgaactattacctacatttga-3' (SEQ ID NO:3)) to the upstream of the luceferase gene in pHD(X3)Luc vector. CV-1 cells were transfected in 96-well plates with the RXR and PPARalpha expression vectors together with the reporter construct. Cells were cultured in media containing the delipidized serum for 24 hours after transfection, then added with tested compounds dissolved in DMSO. The final concentration of DMSO in culture medium (200 ul) was 0.5%. Cells were treated with different compounds in different concentrations for 24 hours, followed by luciferase assay in a plate reader (Fluoroscan, Thermo Life Sciences).

EXAMPLE 31

Figure 2:
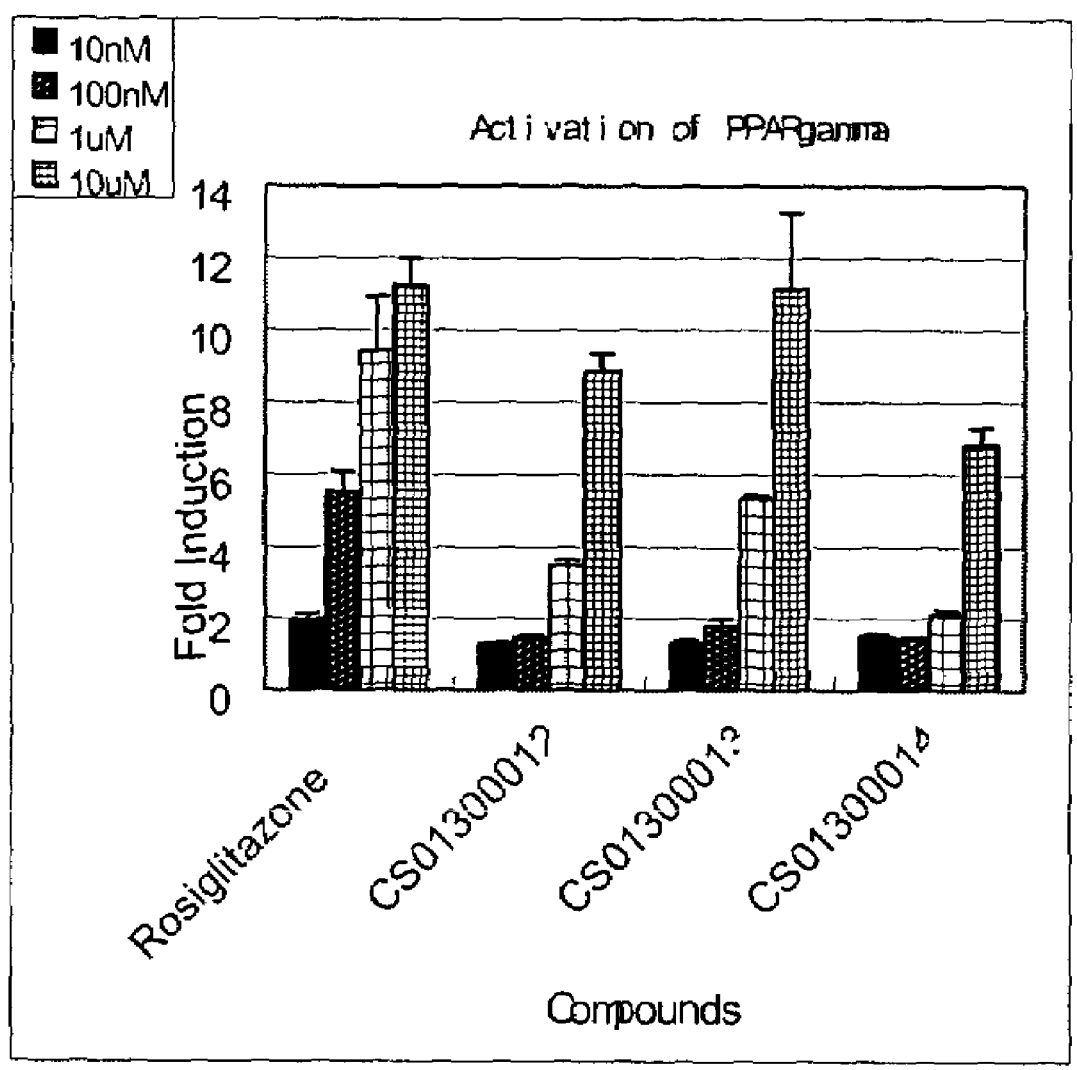
FIG. 2 shows comparative activation of RXR/PPAR gamma heterodimers by compounds of the present invention (Example 31).

Testing of dimethyl 4-[2-(5,6,7,8-tetrahydro-2-naphthoxy)ethoxy]benzylmalonate (compounds CS0130012), 2-(methoxycarbonyl)-3-[4-[2-(5,6,7,8-tetrahydro-2-naphthoxy)ethoxy]phenyl]propionic acid (compound CS01300013) and 2-[4-[2-(5,6,7,8-tetrahydro-2-naphthoxy)ethoxy]benzyl]malonic acid (compound CS01300014) as an RXR/PPARgamma heterodimer agonist in vitro. See, FIG. 2.

Activation of RXR/PPARgamma heterodimer was measured by luciferase reporter assay. Briefly, full length PPARgamma was cloned by PCR using oligonucleotide primers (5'-ggggtacctgcttcagcagcgtgttcga-3' (SEQ ID NO: 4) and 5'-gctctagatgttggcagtggctcaggac-3' (SEQ ID NO: 5)) from adipose tissue. The amplified cDNA was cloned into an expression vector and sequenced. The reporter was constructed by insertion of an annealed oligonucleotide containing 1 copy of the PPAR response element (5'-cgcgttcctttccgaacgtgacctttgtcctggtccccttttgct-3') to the upstream of the luceferase gene. CV-1 cells were transfected in 96-well plates with the RXR and PPARgamma expression vectors together with the reporter construct. Cells were cultured in media containing the delipidized serum for 24 hours after transfection, then added with tested compounds dissolved in DMSO. The final concentration of DMSO in culture medium (200 ul) was 0.5%. Cells were treated with different compounds in different concentrations for 24 hours, followed by luciferase assay in a plate reader (Fluoroscan, Thermo Life Sciences).

EXAMPLE 32

Figure 3:
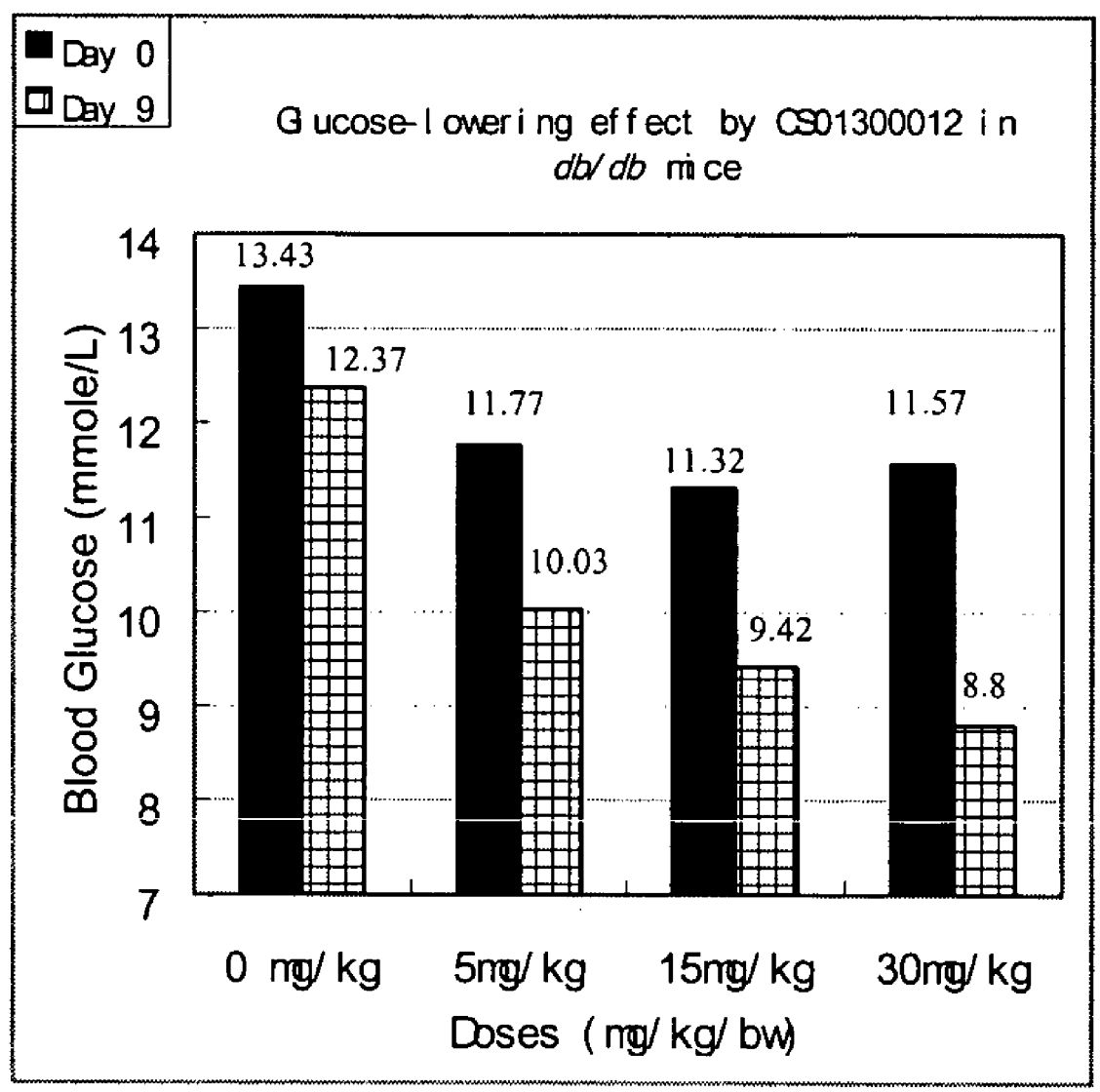
FIG. 3 graphically illustrates in vivo blood glucose lowering affected by a compound of the present invention (Example 32).

The effect of dimethyl 4-[2-(5,6,7,8-tetrahydro-2-naphthoxy)ethoxy]benzylmalonate (Compound CS-01300012) is effective in lowering blood glucose level in db/db mice in vivo. See, FIG. 3.

7 week-old male db/db (C57BLKS/J-m+/+Lepr$^{db}$) mice (n=10) from Jackson Laboratories (Bar Harbor, Me.) were treated once daily with indicated doses of the compound by gavage feeding at each morning for 9 consecutive days. All animals were maintained under standardized conditions (12-hour light/dark cycle, 22° C.). At day 9 of the treatment, blood glucose level was measured after 3 hours fasting after dosing by taking tail blood using Bayer Strips.

EXAMPLE 33

Figure 4:
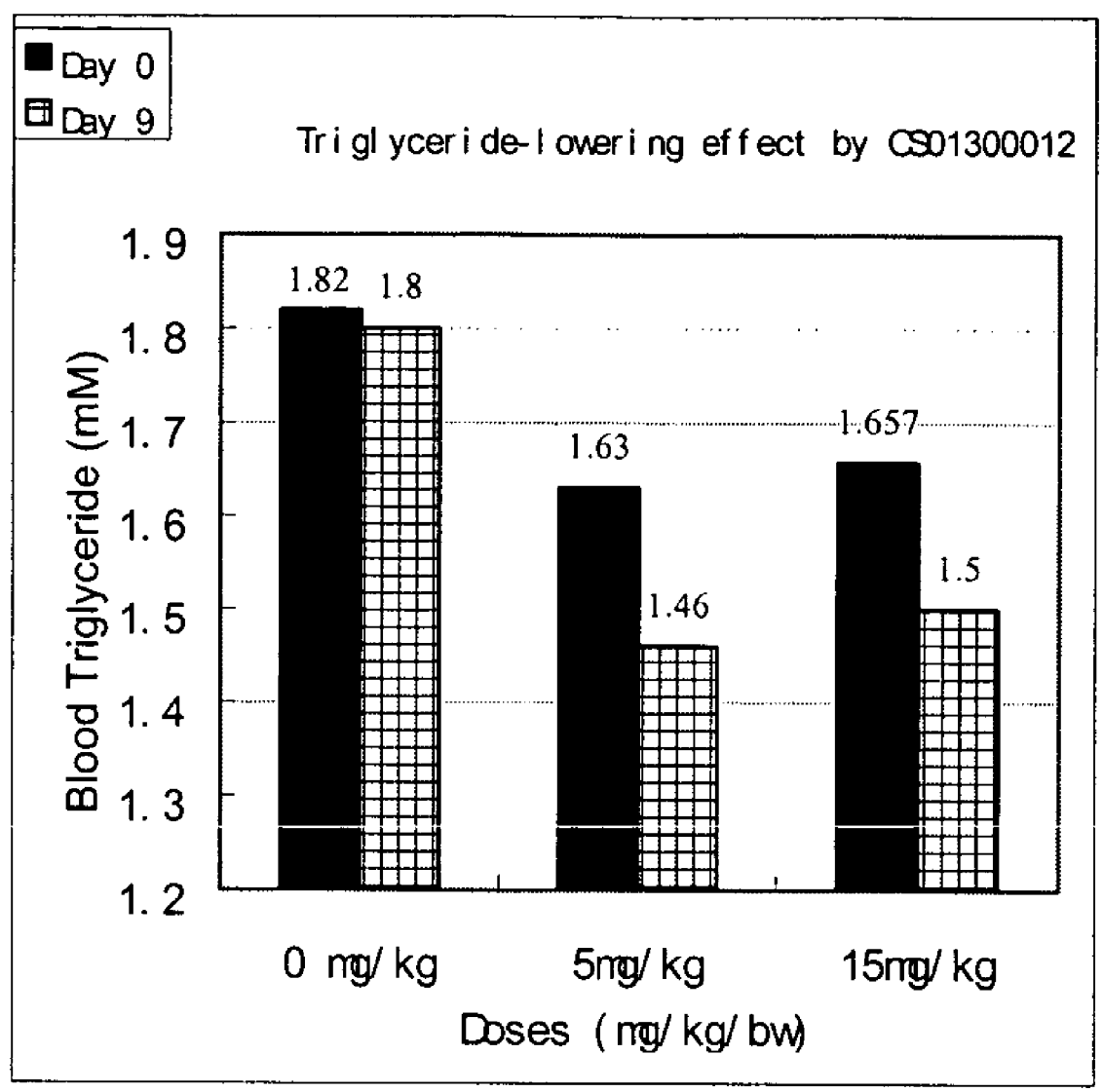
FIG. 4 graphically illustrates in vivo blood triglyceride level lowering affected by a compound of the present invention (Example 33).

The example of compound dimethyl 4-[2-(5,6,7,8-tetrahydro-2-naphthoxy)ethoxy]benzylmalonate (Compound CS-01300012) is effective in lowering blood triglyceride level in db/db mice in vivo. See, FIG. 4.

7 week-old male db/db (C57BLKS/J-m+/+Lepr$^{db}$) mice (n=10) from Jackson Laboratories (Bar Harbor, Me.) were treated once daily with indicated doses of the compound by gavage feeding at each morning for 9 consecutive days. All animals were maintained under standardized conditions (12-hour light/dark cycle, 22° C.). At day 9 of the treatment, blood triglyceride level was measured after 3 hours fasting after dosing by taking tail blood using Roche Strips.

EXAMPLE 34

Figure 5:
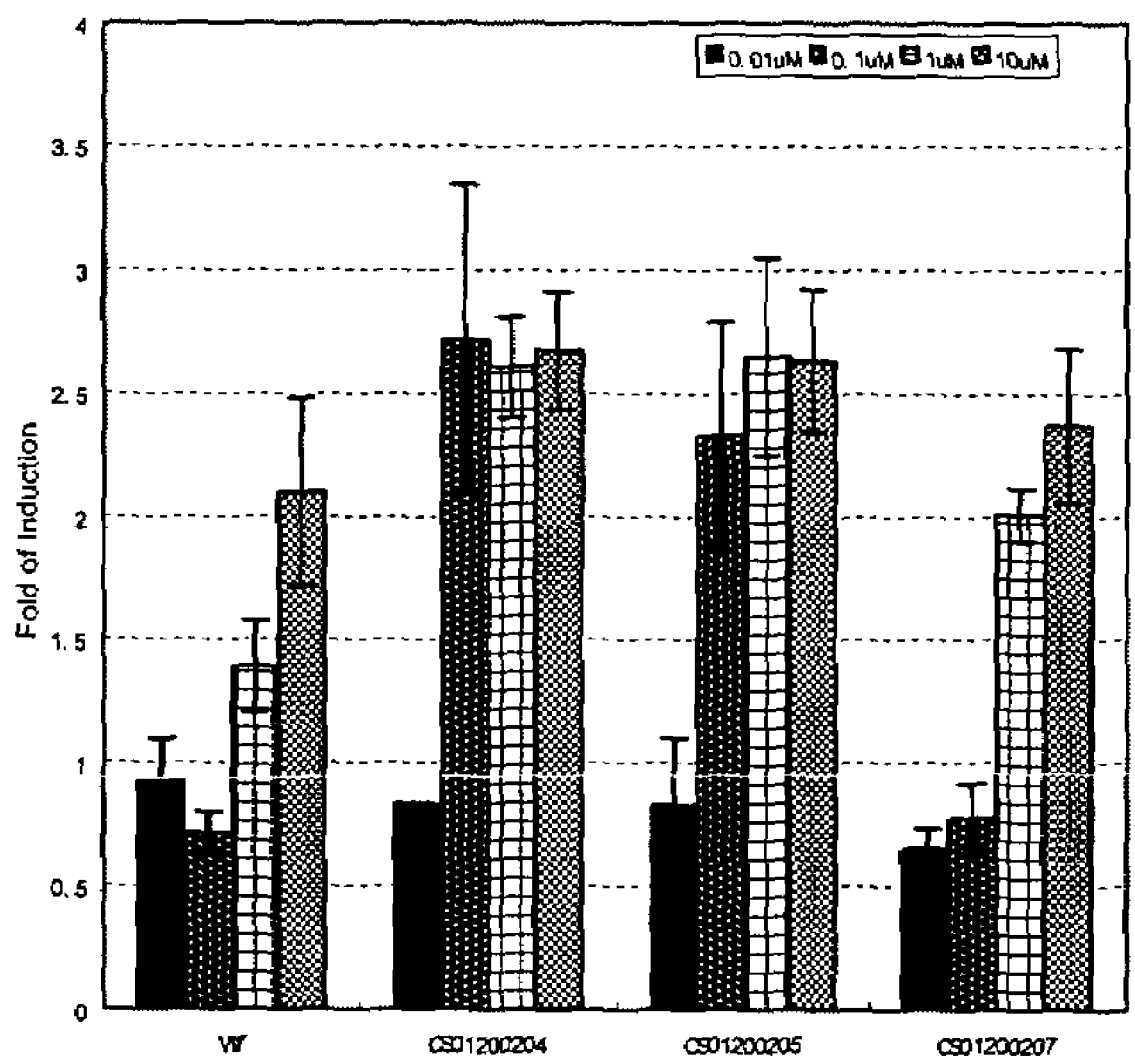
FIG. 5 shows comparative activation of RXR/PPAR alpha heterodimers by compounds of the present invention (Example 34).
Figure 6:
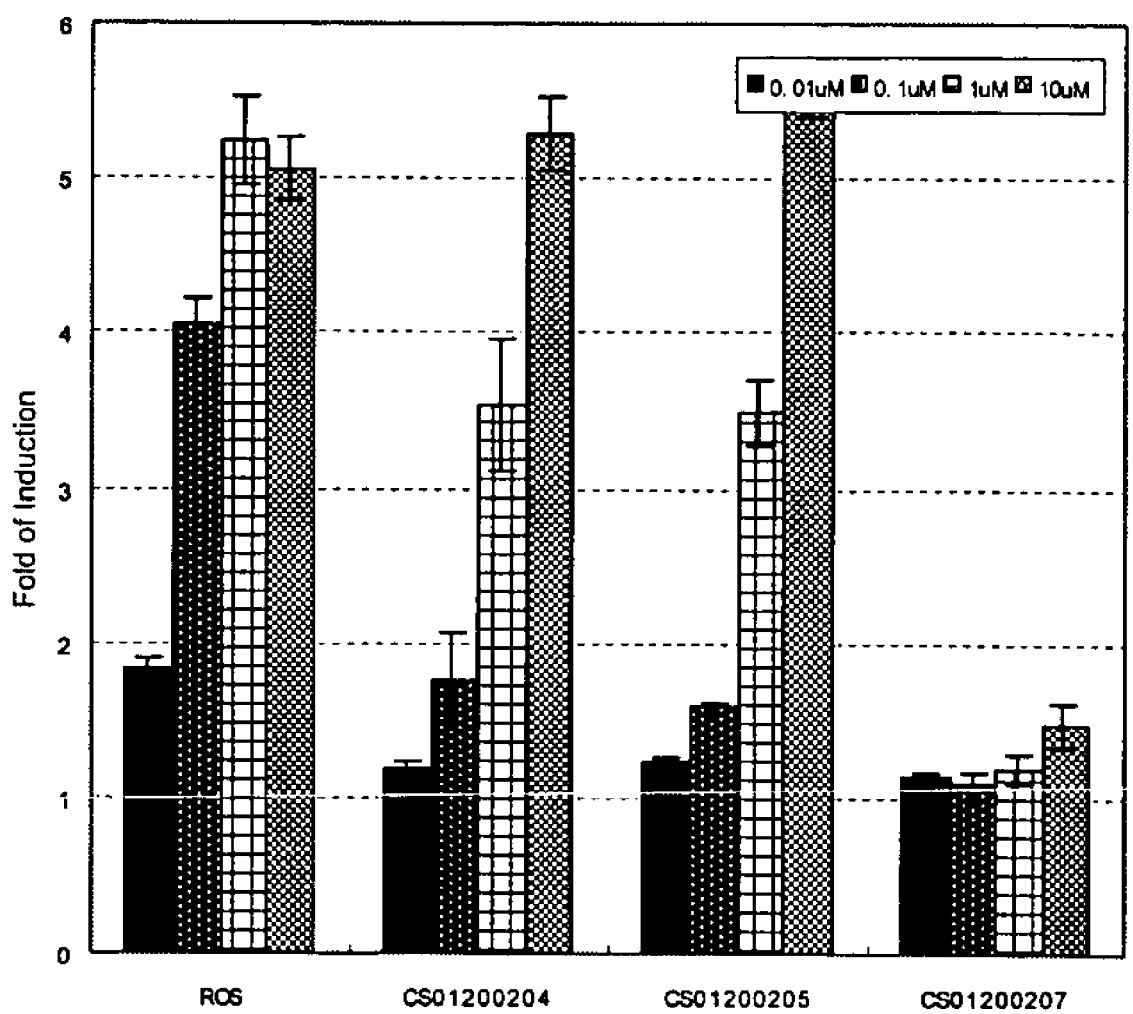
FIG. 6 shows comparative activation of RXR/PPAR gamma heterodimers by compounds of the present invention (Example 34).
Figure 7:
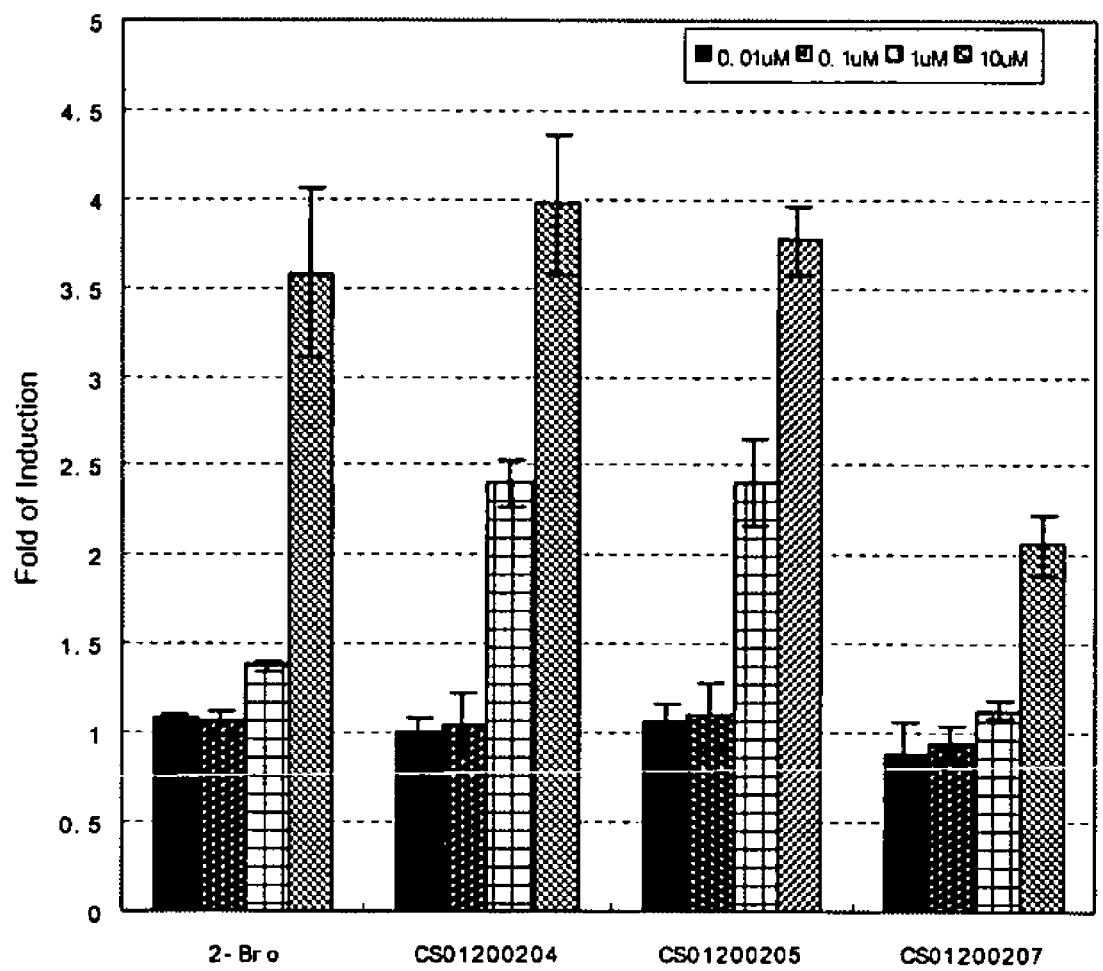
FIG. 7 shows comparative activation of RXR/PPAR delta heterodimers by compounds of the present invention (Example 34).

Testing of dimethyl 4-[2-(2-naphthoxy)ethoxy]benzylmalonate (Lab code CS01200204), 2-(methoxycarbonyl)-3-[4-[2-(2-naphthoxy)ethoxy]phenyl]propionic acid (Lab code CS01200205), 2-carbamoyl-3-[4-[2-(2-naphthoxy)ethoxy]phenyl]propionic acid (Lab code CS01200207) as an RXR/PPARalpha, RXR/PPARgamma, and RXR/PPARdelta heterodimer agonists in vitro. See, FIG. 5 (RXR/PPARalpha), FIG. 6 (RXR/PPARgamma), and FIG. 7 (RXR/PPARdelta).

EXAMPLE 35

Figure 8:
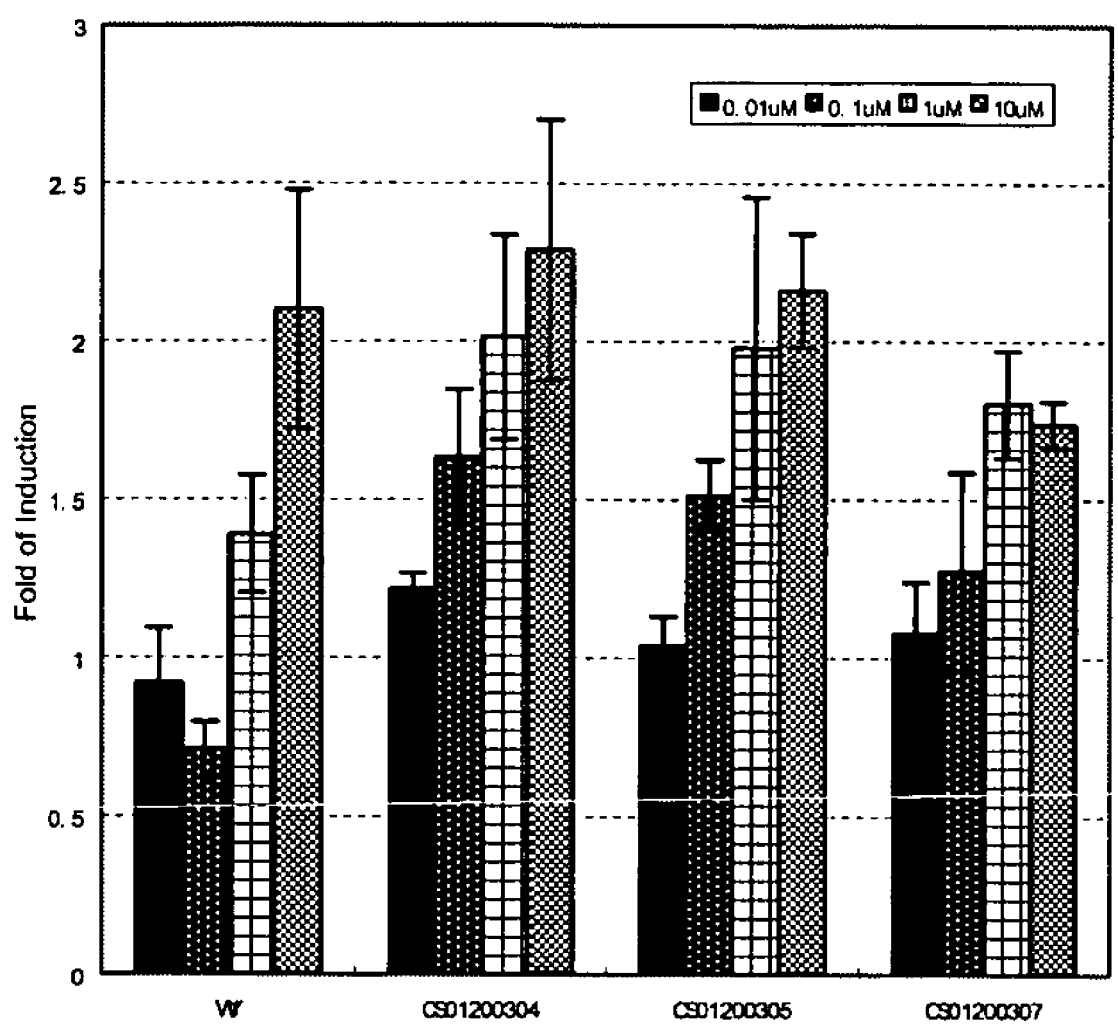
FIG. 8 graphically illustrates comparative activation of RXR/PPAR alpha heterodimers by compounds of the present invention (Example 35).
Figure 9:
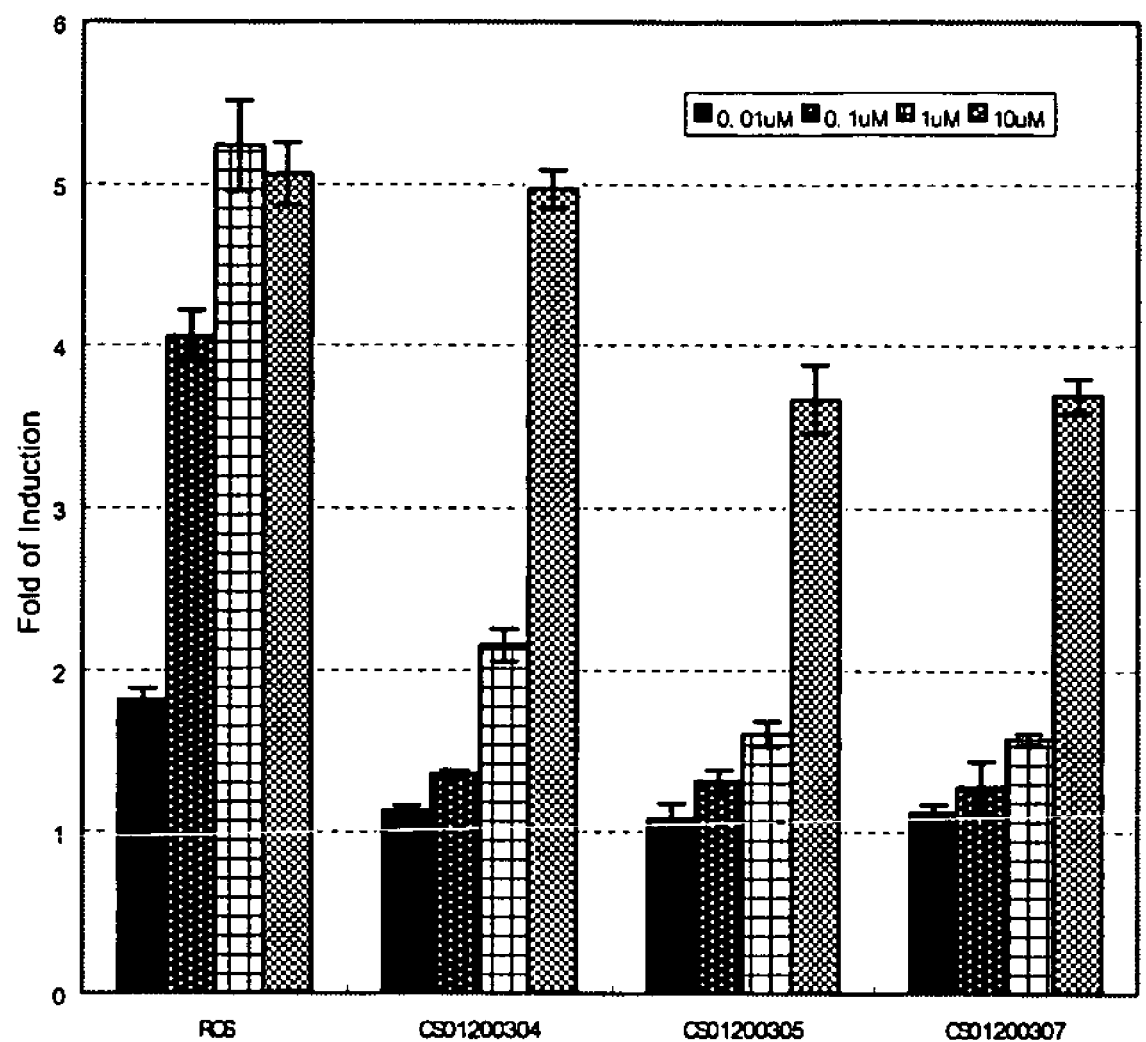
FIG. 9 graphically illustrates comparative activation of RXR/PPAR gamma heterodimers by compounds of the present invention (Example 35).
Figure 10:
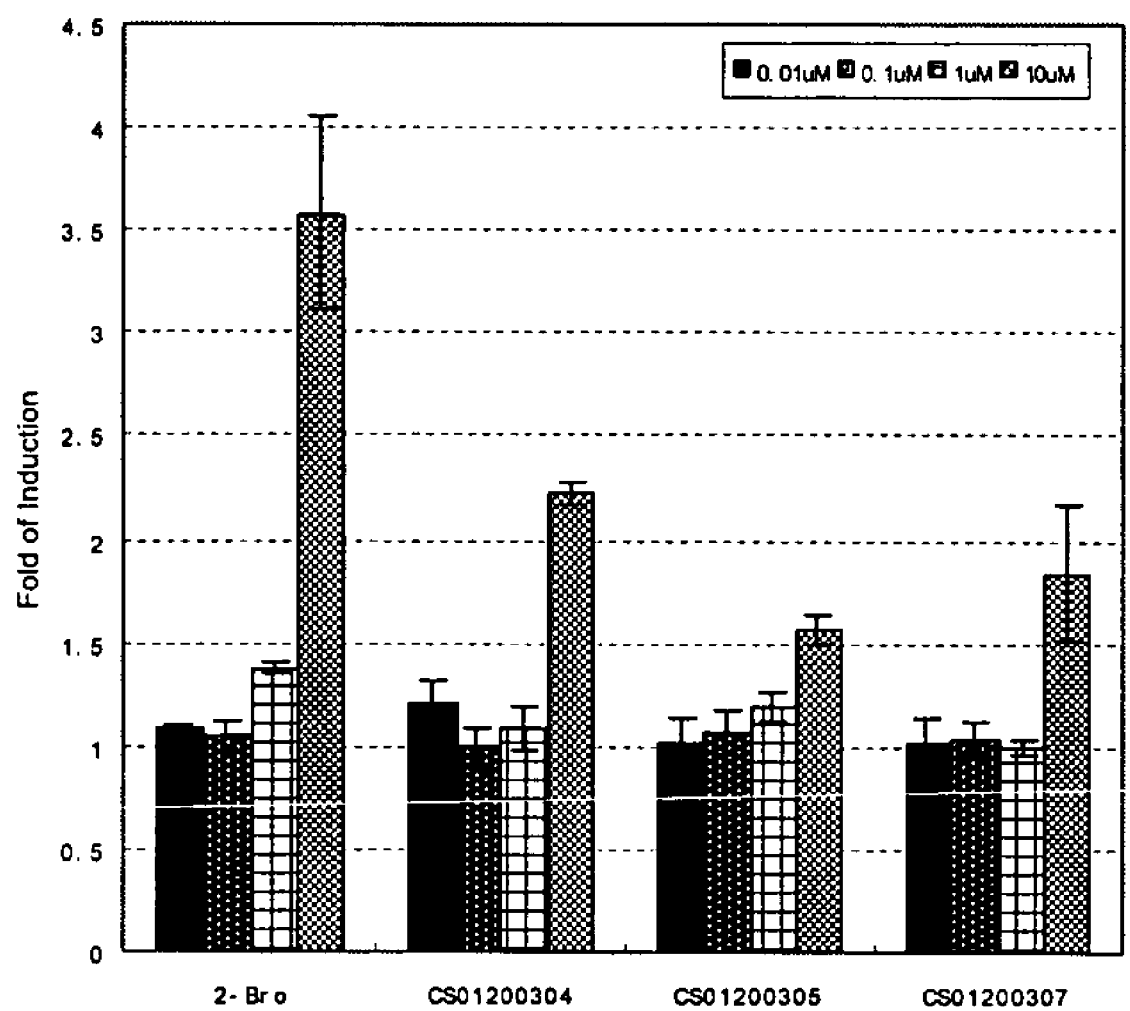
FIG. 10 graphically illustrates comparative activation of RXR/PPAR delta heterodimers by compounds of the present invention (Example 35).

Testing of dimethyl 4-[2-(6-quinolinoxy)ethoxy]benzylmalonate (Lab code CS01200304), 2-(methoxycarbonyl)-3-[4-[2-(6-quinolinoxy)ethoxy]phenyl]propionic acid (Lab code CS01200305), 2-carbamoyl-3-[4-[2-(6-quinolinoxy)ethoxy]phenyl]propionic acid (Lab code CS01200307) as an RXR/PPARalpha, RXR/PPARgamma, and RXR/PPARdelta heterodimer agonists in vitro. See, FIG. 8 (RXR/PPARalpha), FIG. 9 (RXR/PPARgamma), and FIG. 10 (RXR/PPARdelta).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described compositions and modes for carrying out the invention which are obvious to those skilled in the art or related fields are intended to be within the scope of the following claims.

What is claimed is:

1. A compound of formula I prepared for administration

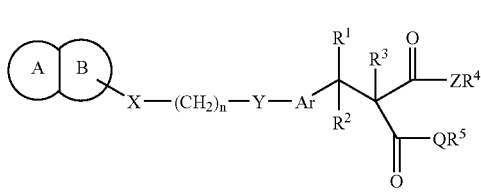

wherein
ring A, fused to ring B, represents a 6 membered cyclic ring, which may optionally contain one nitrogen atom and may optionally be substituted with one or more alkyl; the ring A may be saturated or aromatic;
ring B, fused to ring A, is a benzene ring;
X and Y are independently O;
Z represents O or $NR^6$ wherein $R^6$ represents hydrogen or alkyl;
Q represents O or $NR^7$ wherein $R^7$ represents hydrogen or alkyl;
$R^1$, $R^2$ and $R^3$ are independendy H or alkyl;
$R^4$, $R^5$ are independently H or alkyl;
Ar represents benzene; and
n is an integer ranging from 1 to 6.

2. The compound of claim 1, wherein n is 2.

3. The compound of claim 1, wherein
Q is O or $NH^7$ wherein $R^7$ represents hydrogen;
$R^1$, $R^2$ and $R^3$ are independently H;
$R^4$ and $R^5$ are independently H or methyl;
Ar is benzene group;
n is 2.

4. A compound of formula II wherein ring A, ring B, X, Y, Ar and n are as defined in claim 1, and T is —CHO or —R₁C=C(COOMe)₂ wherein $R^1$ is as defined in claim 1.

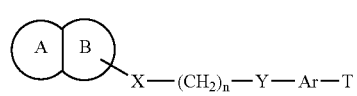

5. The compound according to claim 4 wherein:
n is 2.

6. A process for the preparation of a compound according to claim 1, a stereoisomer, enantiomer, diastereomer, hydrate or pharmaceutically acceptable salt thereof comprising the steps of:
a) changing the compound of formula I to the benzaldehyde derivative 2;

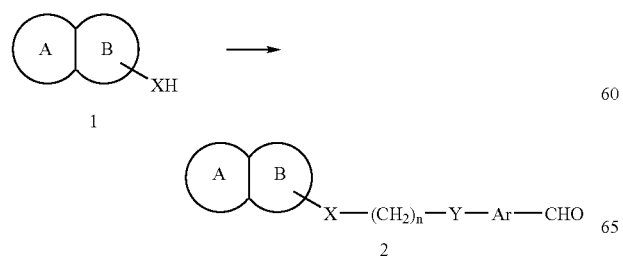

b) changing the aldehyde 2 to the benzylidene 3 by Knoevenagel condensation;

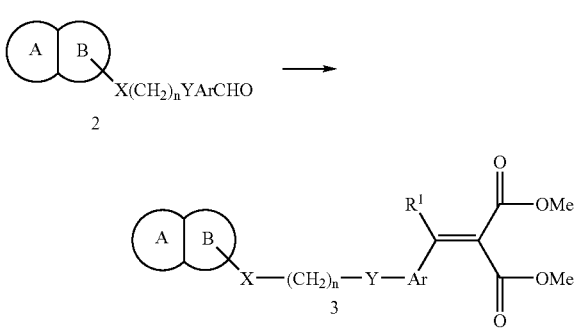

c) obtaining the dimethyl malonate 4 by catalytic hydrogenation of 3;

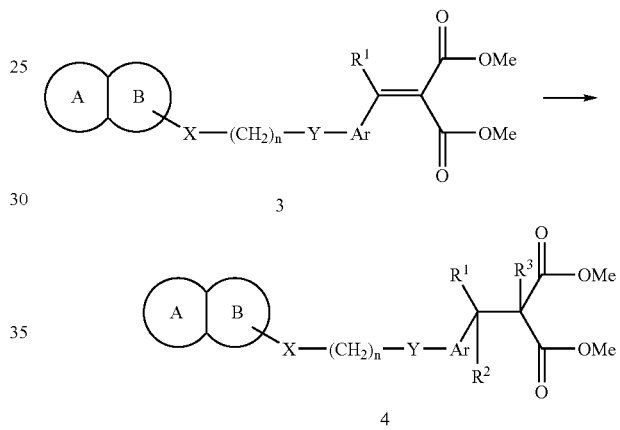

d) changing the dimethyl malonate 4 to other 1,3-dicarbonyl compounds 5.

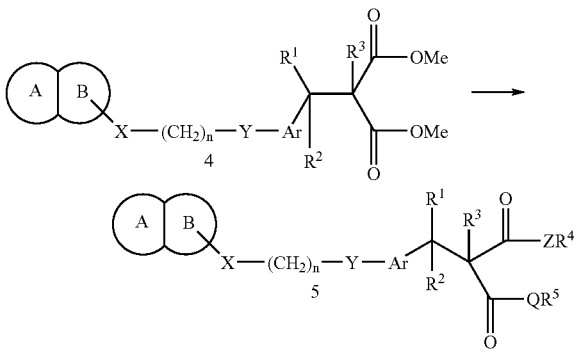

7. The process according to claim 6 wherein:
(a) the benzaldehyde derivative 2 is prepared by the reaction of compound 1 with p-bromoethoxy benzaldehyde in the presence of potassium hydroxide;
(b) the Knoevenagel condensation is achieved by treating the benzaldehyde 2 with dimethyl malonate in the presence of a catalytic quantity of piperidinium acetate;

(c) the catalytic hydrogenation is achieved by treating the benzylidene 3 with $H_2$ in the presence of 5% palladium on carbon;

(d) the other 1,3-dicarbonyl compounds 5 are prepared from 4 by hydrolysis or other conventional reactions.

8. A pharmaceutical composition for activating nuclear receptors comprising an effective amount of a compound according to claim 1 wherein the composition further comprises one or more pharmaceutically acceptable excipients, carriers or diluents.

9. The pharmaceutical composition according to claim 8, wherein the nuclear receptors comprise the Retinoid X Receptor (RXR), and the Peroxisome Proliferator-Activated Receptors (PPAR).

10. The pharmaceutical composition of claim 9 in unit dosage form, comprising from about 0.05 to about 100 mg of the active compound.

11. The pharmaceutical composition of claim 10 in unit dosage form, comprising from about 0.1 to about 50 mg of the active compound.

12. The pharmaceutical composition of claim 9 which is suitable for administration by an oral, nasal, transdermal, pulmonary, or parenteral route.

13. A method of treating a condition characterized by hyperglycemia comprising administering to a subject in need thereof an effective amount of a compound according to claim 1 to lower blood glucose.

14. A method according to claim 13 wherein at least one condition is selected from the group consisting of type 2 diabetes, dyslipidemia, and obesity.

15. The method according to claim 14, wherein the effective amount of the compound is in the range of from about 0.05 to about 100 mg/kg body weight per day.

16. The method according to claim 14, wherein the effective amount of the compound is in the range of from about 0.1 to about 50 mg/kg body weight per day.

* * * * *